(12) United States Patent
Seger et al.

(10) Patent No.: US 10,246,488 B2
(45) Date of Patent: *Apr. 2, 2019

(54) USE OF INHIBITORY PEPTIDES FOR THE TREATMENT OF INFLAMMATORY DISEASES

(71) Applicant: Yeda Research and Development Co. Ltd., Rehovot (IL)

(72) Inventors: Rony Seger, Rehovot (IL); Eldar Zehorai, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/623,433

(22) Filed: Jun. 15, 2017

(65) Prior Publication Data

US 2017/0283457 A1 Oct. 5, 2017

Related U.S. Application Data

(62) Division of application No. 14/778,624, filed as application No. PCT/IL2014/050376 on Apr. 24, 2014, now Pat. No. 9,714,268.

(60) Provisional application No. 61/815,805, filed on Apr. 25, 2013.

(51) Int. Cl.
| | |
|---|---|
| C07K 7/06 | (2006.01) |
| C07K 7/08 | (2006.01) |
| A61K 38/00 | (2006.01) |
| A61K 38/08 | (2006.01) |
| A61K 47/54 | (2017.01) |

(52) U.S. Cl.
CPC ............. *C07K 7/06* (2013.01); *A61K 38/08* (2013.01); *A61K 47/543* (2017.08); *C07K 7/08* (2013.01); *A61K 38/00* (2013.01)

(58) Field of Classification Search
CPC .. A61K 38/00; A61K 38/08; A61K 47/48046; C07K 7/06; C07K 7/08
See application file for complete search history.

(56) References Cited

U.S. PATENT DOCUMENTS

| | | | |
|---|---|---|---|
| 5,783,664 A | | 7/1998 | Lee et al. |
| 9,714,268 B2* | | 7/2017 | Seger ............... C07K 7/06 |
| 2008/0305493 A1 | | 12/2008 | Strovel et al. |
| 2010/0099627 A1 | | 4/2010 | Seger et al. |
| 2016/0052967 A1 | | 2/2016 | Seger et al. |

FOREIGN PATENT DOCUMENTS

WO WO 2014/174520 10/2014

OTHER PUBLICATIONS

Structural Genomics Consortium et al. Protein production and purification. Nature Methods, 2008. vol. 5 No. 2, pp. 135-146. (Year: 2008).*
Communication Pursuant to Article 94(3) EPC dated Mar. 17, 2017 From the European Patent Office Re. Application No. 14788545.3. (3 Pages).
International Search Report and the Written Opinion dated Jul. 29, 2014 From the International Searching Authority Re. Application No. PCT/IL2014/050376.
Notice of Allowance dated Mar. 3, 2017 From the US Patent and Trademark Office Re. U.S. Appl. No. 14/778,624. (8 pages).
Official Action dated Sep. 21, 2016 From the US Patent and Trademark Office Re. U.S. Appl. No. 14/778,624.
Supplementary European Search Report and the European Search Opinion dated Aug. 8, 2016 From the European Patent Office Re. Application No. 14788545.3.
Chuderland et al. "Identification and Characterization of a General Nuclear Translocation Signal in Signaling Proteins", Molecular Cell, 31: 850-861, Sep. 26, 2008.
Gong et al. "Mechanisms Regulating the Nuclear Translocation of P38 MAP Kinase", Journal of Cellular Biochemistry, XP055291388, 110(6): 1420-1429, May 12, 2010. p. 1428, r-h Col.
Gupta et al. "Dual Function of P38? MAPK in Colon Cancer: Suppression of Colitis-Associated Tumor Initiation but Requirement for Cancer Cell Survival", Cell Press, 25(4): 484-500, Apr. 14, 2014.
Mungall et al. "SubName: Full=Mitogen-Activated Protein Kinase 14", Retrieved from EBI, UniProtKB/TrEMBL Database [Online], XP002760260, Database Accession No. H7C4E2_Human, 1 P., Apr. 18, 2012.
Plotnikov et al. "Nuclear Extracellular Signal-Regulated Kinase 1 and 2 Translocation Is Mediated by Casein Kinase 2 and Accelerated by Autophosphorylation", Molecular and Cellular Biology, 31(17): 3515-3530, Sep. 2011.
Plotnikov et al. "The MAPK Cascades: Signaling Components, Nuclear Roles and Mechanisms of Nuclear Translocation", Biochimica et Biophysica Acta, BBA, XP055289128, 1813(9): 1619-1633, Published Online Dec. 16, 2010.
Wood et al. "Nuclear Localization of p38 MAPK in Response to DNA Damage", International Journal of Biological Science, 5(5): 428-437, Jun. 16, 2009.
Zehorai et al. "Beta-Like Importins Mediate the Nuclear Translocation of Mitogen- Activated Protein Kinases", Molecular and Cellular Biology, XP055289125, 34(2): 259-270, Nov. 11, 2013.
Notification of Office Action and Search Report dated Aug. 24, 2018 From the State Intellectual Property Office of the People's Republic of China Re. Application No. 201480036061.1 and Its Translation Into English. (16 Pages).

* cited by examiner

*Primary Examiner* — Marcela M Cordero Garcia

(57) ABSTRACT

An isolated peptide is disclosed which comprises an amino acid sequence being at least 80% homologous to the sequence as set forth in SEQ ID NO: 1 (PERYQNLSPV), the isolated peptide comprising a nuclear targeting activity, the peptide being no longer than 20 amino acids.

14 Claims, 27 Drawing Sheets
(7 of 27 Drawing Sheet(s) Filed in Color)

Specification includes a Sequence Listing.

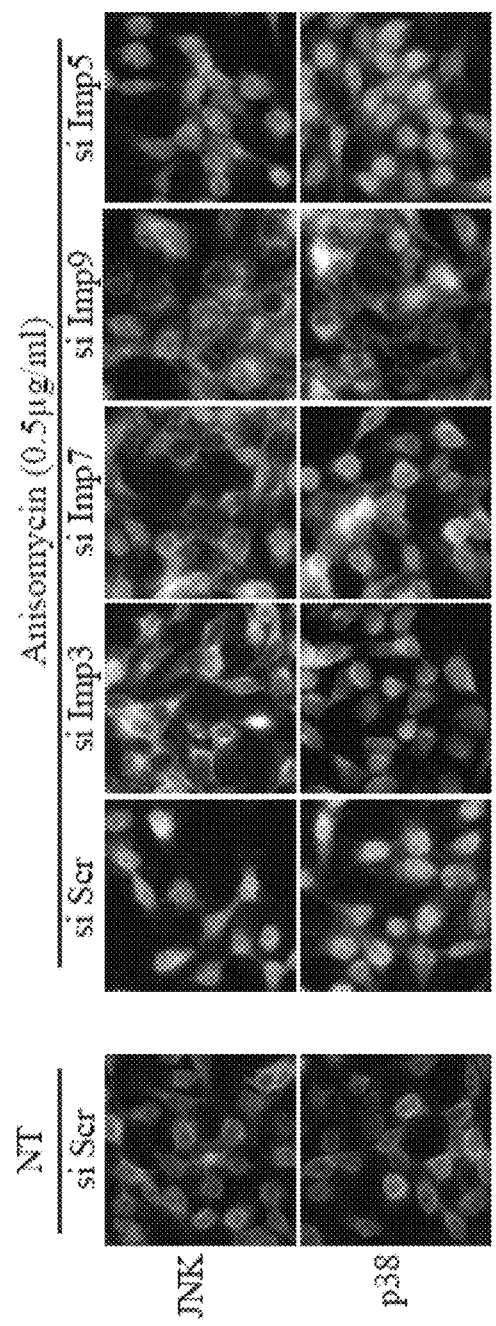

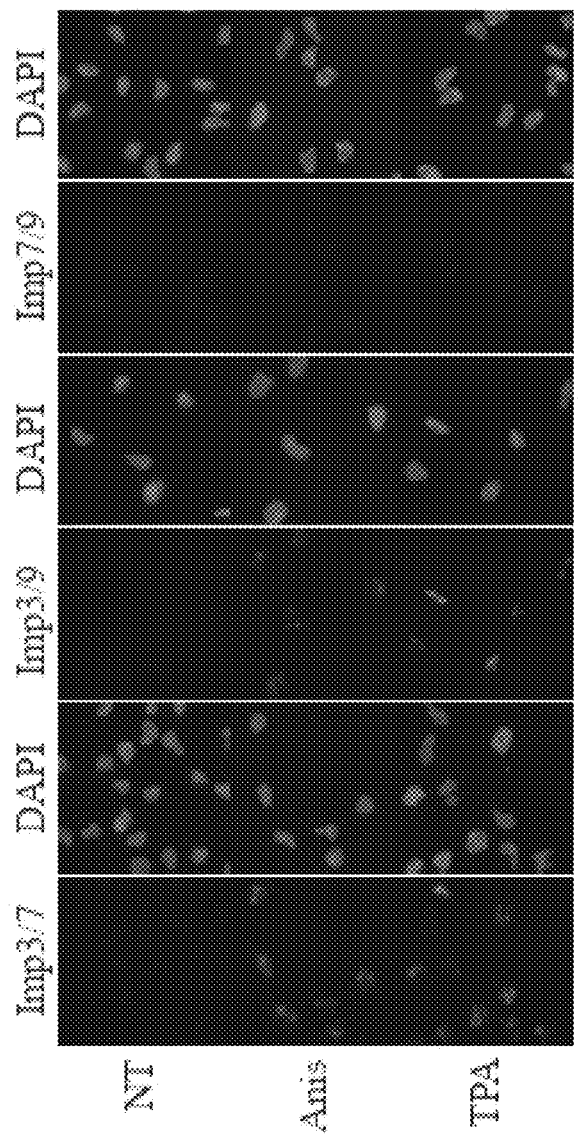

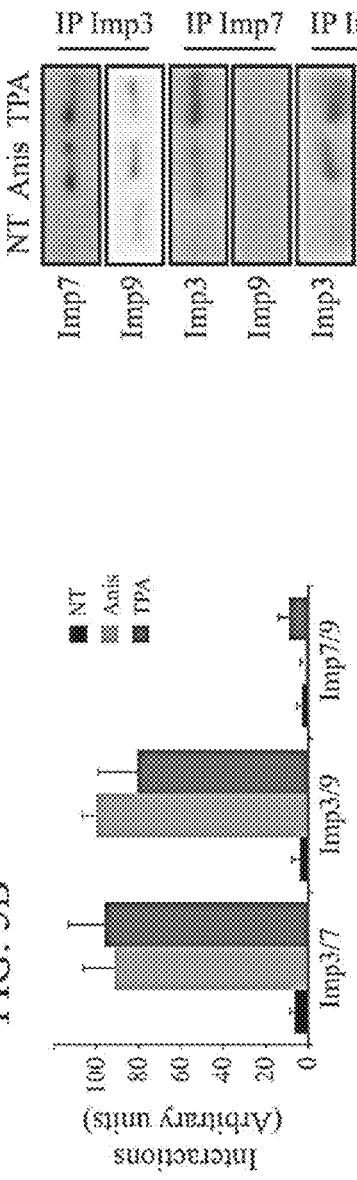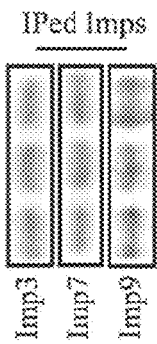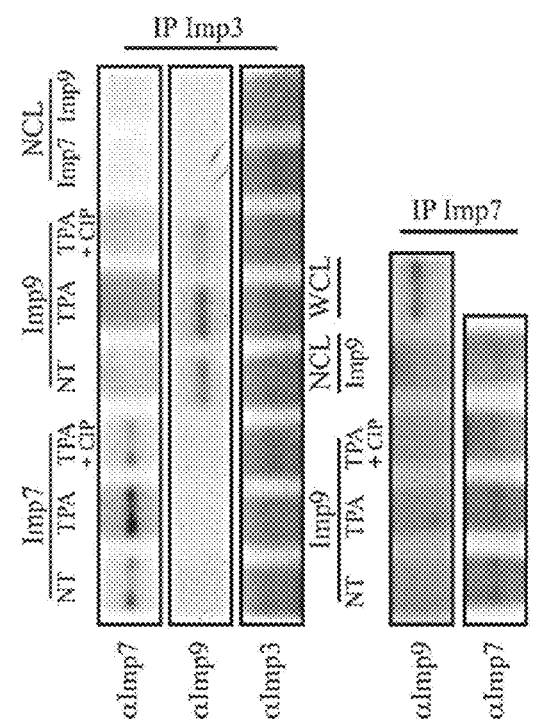

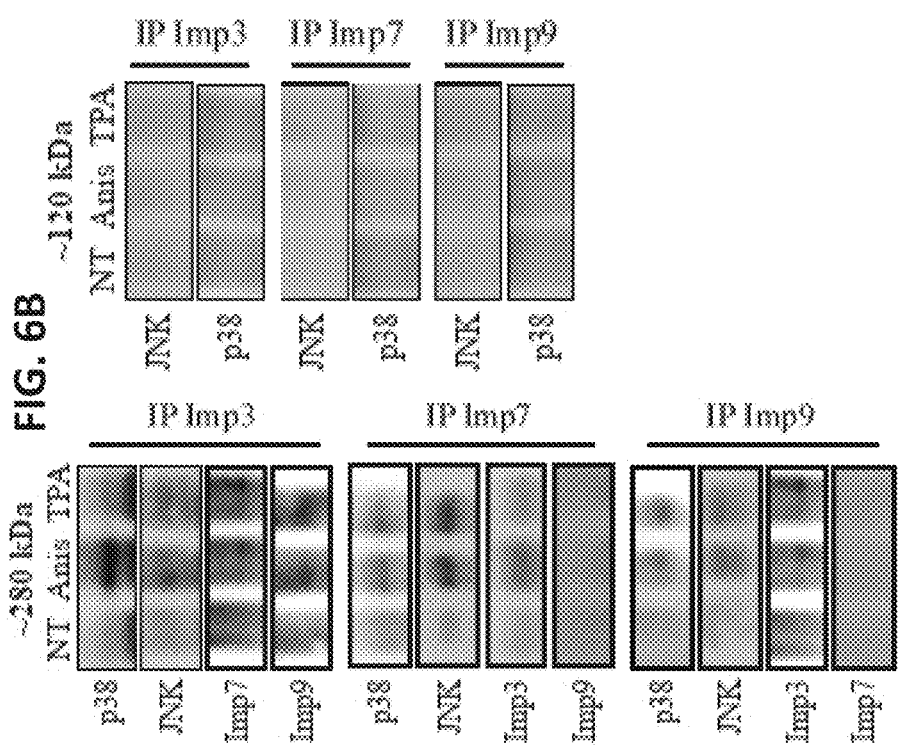

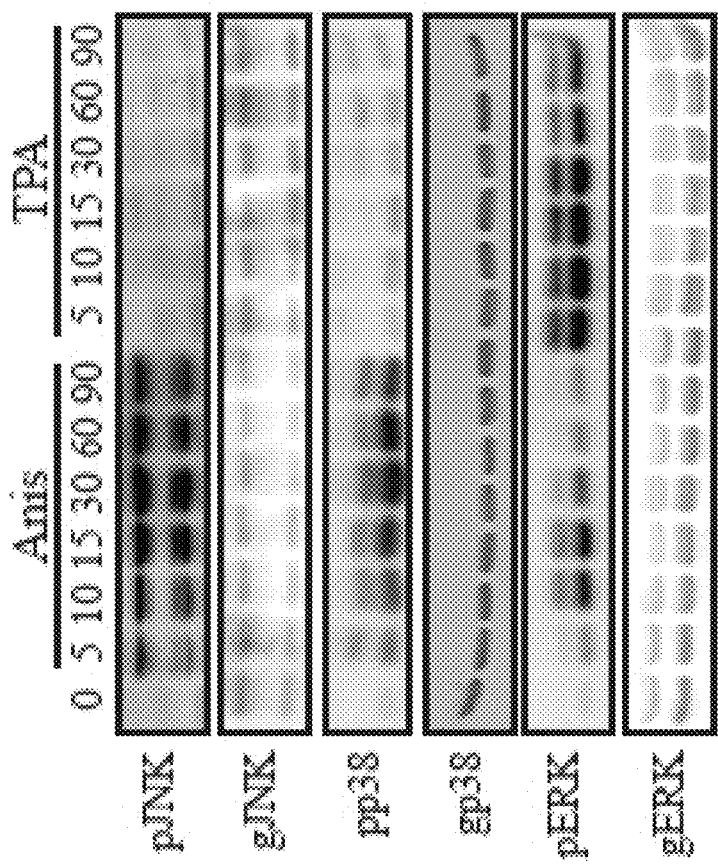

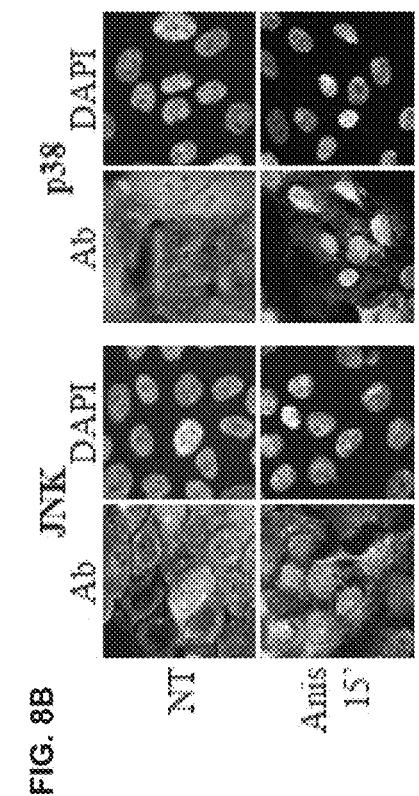
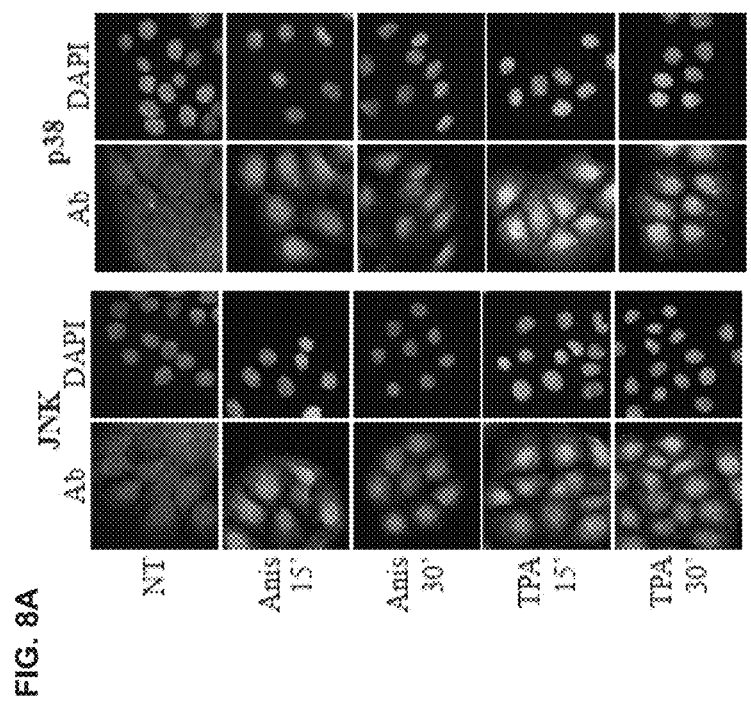
FIG. 8B
FIG. 8A

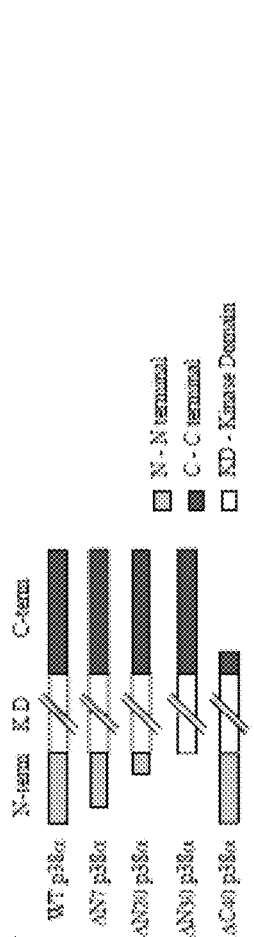
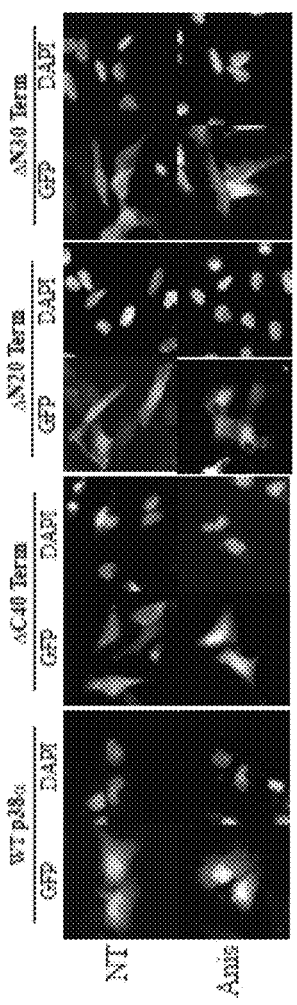
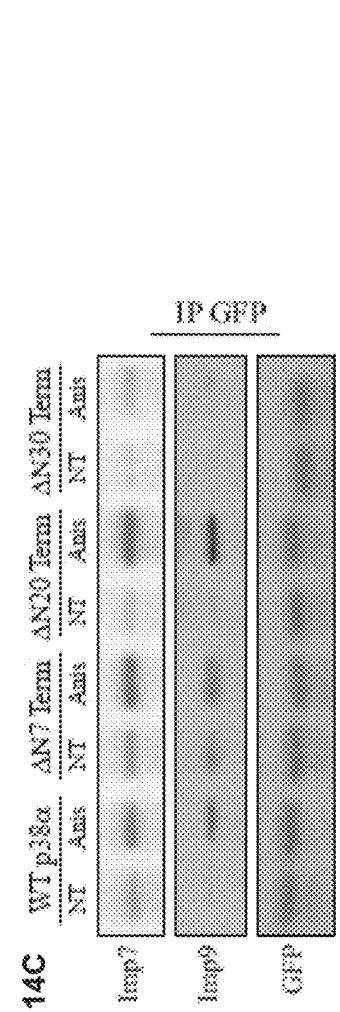
FIG. 14A
FIG. 14B
FIG. 14C

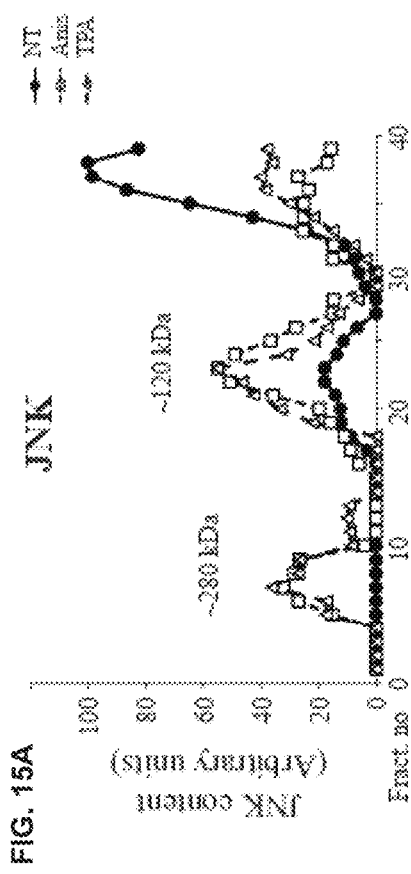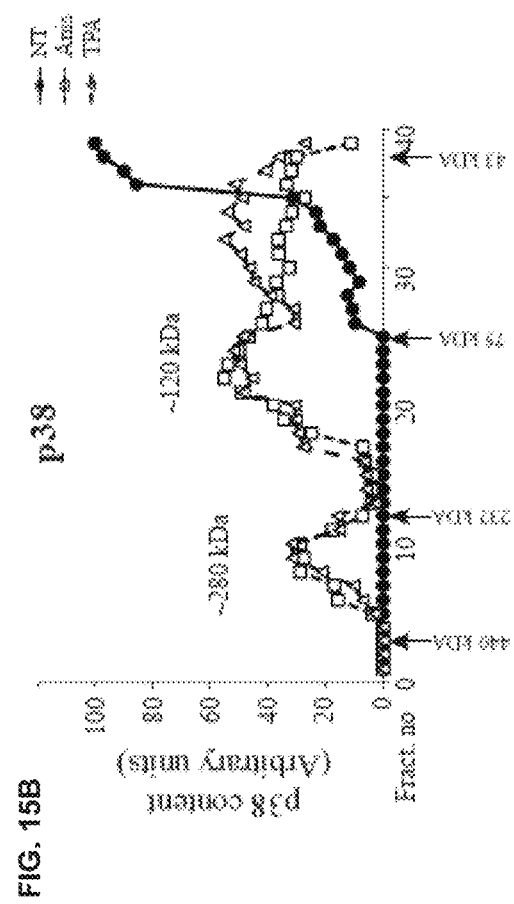
FIG. 15A
FIG. 15B

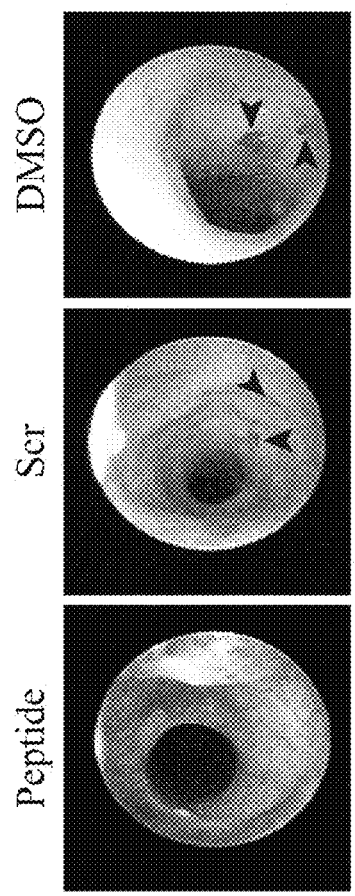
FIG. 17A
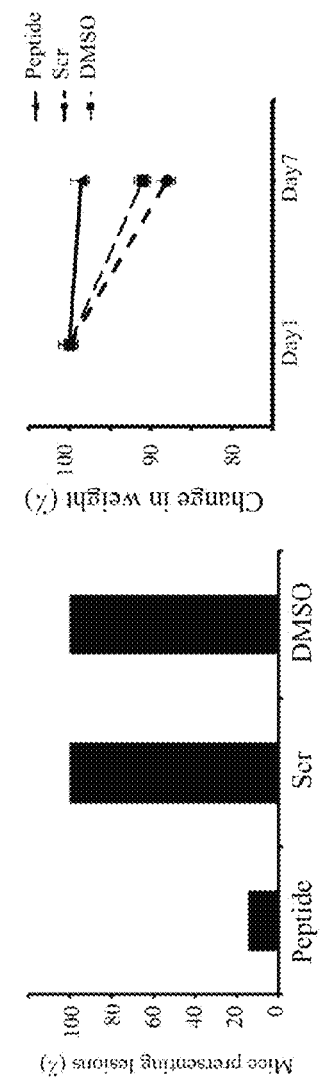
FIG. 17C
FIG. 17B

FIG. 18A  Peptide - KPERYQNLSPVGSGA
New peptide - KPERYQNLSPVAAAA

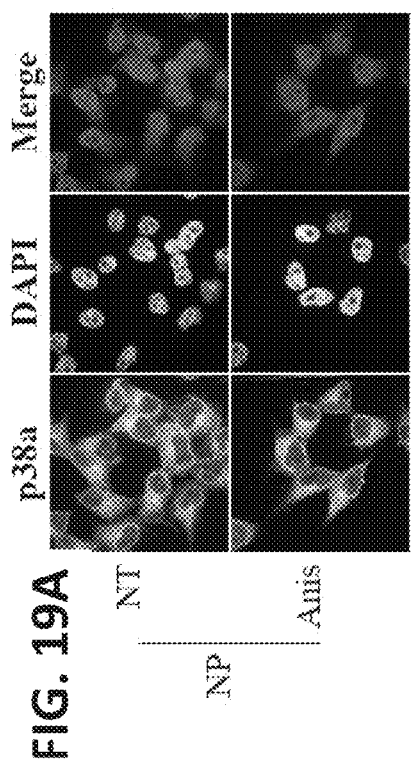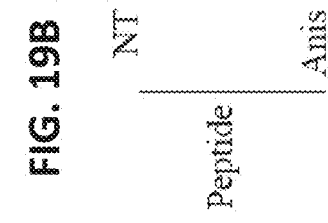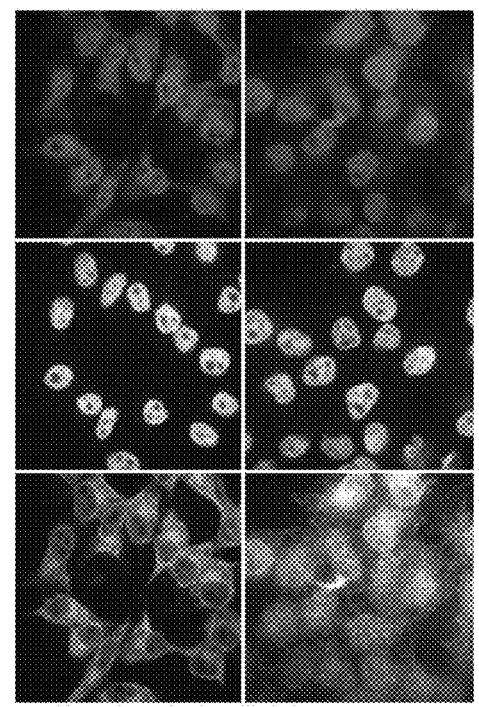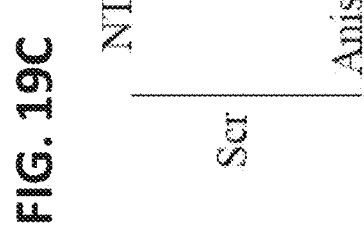
FIG. 19A
FIG. 19B
FIG. 19C

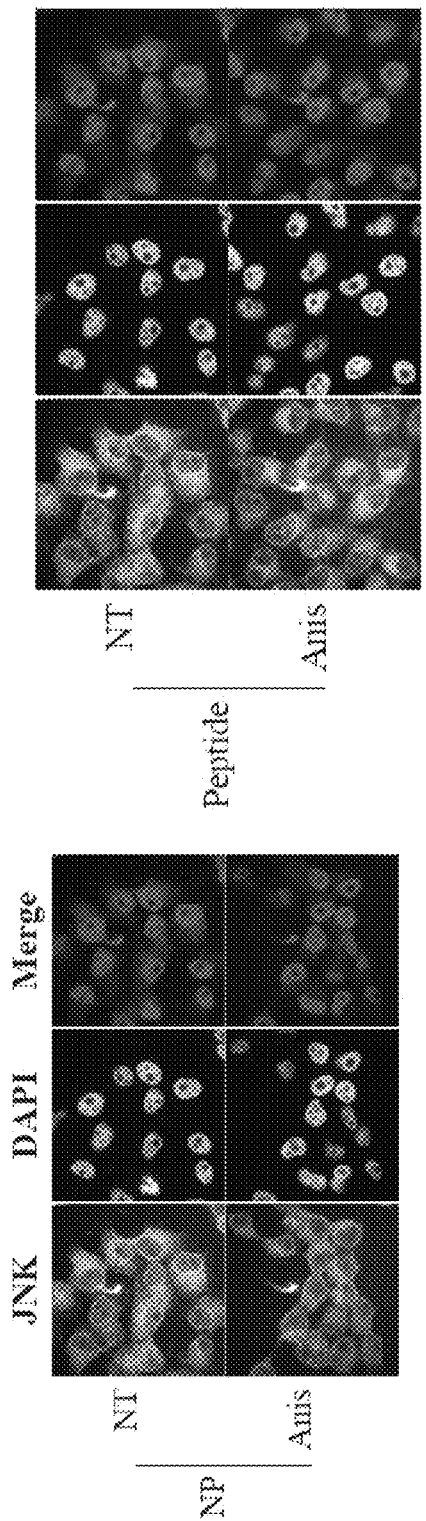
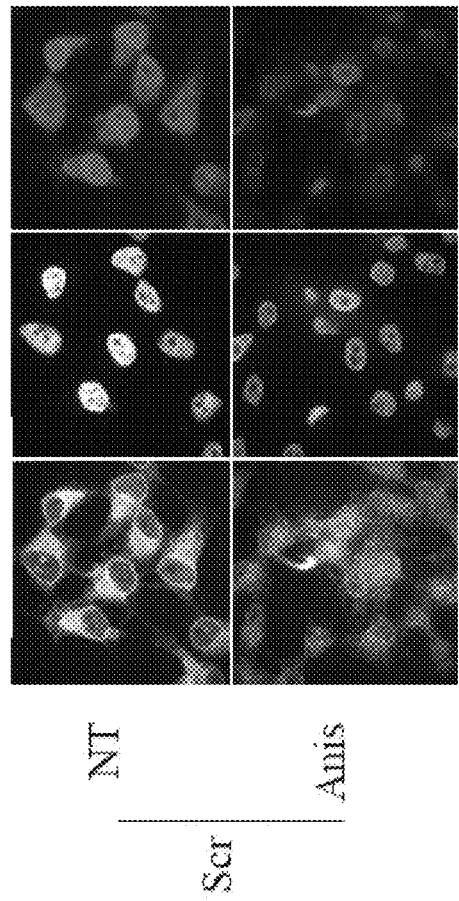
FIG. 20A
FIG. 20B
FIG. 20C

SEQUENCE LISTING

```
<160> NUMBER OF SEQ ID NOS: 16

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Pro Glu Arg Tyr Gln Asn Leu Ser Pro Val
1               5                   10

<210> SEQ ID NO 2
<211> LENGTH: 11
<212> TYPE: PRT
<213> ORGANISM: Artificial sequence
<220> FEATURE:
<223> OTHER INFORMATION: Synthetic peptide

<400> SEQUENCE: 2

Pro Glu Arg Tyr Gln Asn Leu Ser Pro Val Gly
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Pro Glu Arg Tyr Gln Asn Leu Ser Pro Val Gly Ser
1               5                   10
```

-continued

```
<210> SEQ ID NO 4
<211> LENGTH: 13
<212> TYPE: PRT
<213> ORGANISM: Artificial sequence
<220> FEATURE:
<223> OTHER INFORMATION: Synthetic peptide

<400> SEQUENCE: 4

Pro Glu Arg Tyr Gln Asn Leu Ser Pro Val Gly Ser Gly
1               5                   10

<210> SEQ ID NO 5
<211> LENGTH: 14
<212> TYPE: PRT
<213> ORGANISM: Artificial sequence
<220> FEATURE:
<223> OTHER INFORMATION: Synthetic peptide

<400> SEQUENCE: 5

Pro Glu Arg Tyr Gln Asn Leu Ser Pro Val Gly Ser Gly Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Lys Pro Glu Arg Tyr Gln Asn Leu Ser Pro Val Gly Ser Gly Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Lys Pro Glu Arg Tyr Gln Asn Leu Ser Pro Val Ala Ala Ala Ala
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Lys Pro Glu Arg Tyr Gln Asn Leu Ser Pro Val
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 9

Lys Pro Glu Arg Tyr Gln Asn Leu Ser Pro Val Gly Ser Gly Ala
1               5                   10                  15
```

```
<210> SEQ ID NO 10
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 10

Lys Pro Glu Arg Tyr Gln Asn Leu Ser Pro Val Ala Ala Ala Ala
1               5                   10                  15

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 11

Lys Pro Glu Arg Tyr Gln Asn Leu Ser Pro Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 12

Pro Glu Arg Tyr Gln Asn Leu Ser Pro Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 13

Pro Glu Arg Tyr Gln Asn Leu Ser Pro Val Gly
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 14

Pro Glu Arg Tyr Gln Asn Leu Ser Pro Val Gly Ser
1               5                   10
```

```
<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 15

Pro Glu Arg Tyr Gln Asn Leu Ser Pro Val Gly Ser Gly
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Myristoylated peptide

<400> SEQUENCE: 16

Pro Glu Arg Tyr Gln Asn Leu Ser Pro Val Gly Ser Gly Ala
1               5                   10
```

USE OF INHIBITORY PEPTIDES FOR THE TREATMENT OF INFLAMMATORY DISEASES

RELATED APPLICATIONS

This application is a division of U.S. patent application Ser. No. 14/778,624 filed on Sep. 21, 2015, which is a National Phase of PCT Patent Application No. PCT/IL2014/050376 having International Filing Date of Apr. 24, 2014, which claims the benefit of priority under 35 USC § 119(e) of U.S. Provisional Patent Application No. 61/815,805 filed on Apr. 25, 2013. The contents of the above applications are all incorporated by reference as if fully set forth herein in their entirety.

SEQUENCE LISTING STATEMENT

The ASCII file, entitled 70290SequenceListing.txt, created on Jun. 15, 2017, comprising 4,348 bytes, submitted concurrently with the filing of this application is incorporated herein by reference.

FIELD AND BACKGROUND OF THE INVENTION

The present invention relates to peptides that may be used to prevent nuclear translocation of proteins which naturally associate with Imp7 as a means for translocating into the nucleus. The peptides may be used for the treatment of inflammatory and immune diseases. Further, the peptides may be used to promote nuclear translocation of proteins and other compounds into the cell nucleus when attached thereto.

To ensure accurate cellular functioning, the spatial distribution of proteins needs to be tightly regulated and coordinated. This is particularly apparent in many signaling proteins that dynamically and rapidly change their localization upon extracellular stimulation. In order to maintain such regulation, the nucleus is separated from the cytoplasm by a double membrane envelope that allows for a selective entrance of proteins through specialized nuclear pore complexes (NPC). The selectivity of nuclear localization is primarily mediated by a nuclear localization signal (NLS) harbored within the sequence of the nuclear protein [G. Schlenstedt, FEBS Lett 389, 75 (Jun. 24, 1996)].

The major type of NLS identified thus far is composed of basic amino acids which are required for the mechanism of entrance through the NPC. These basic sequences come in two flavors: (i) a single stretch of five to six basic amino acids, exemplified by the simian virus (SV) 40 large T antigen NLS; and (ii) a bipartite NLS composed of two basic amino acids, a spacer region of 10-12 amino acids, and a cluster in which three of five amino acids must be basic. This type is typified by nucleoplasmin. For NLS-mediated nuclear import to occur, the NLS first associates with the cytosolic import-receptor proteins importin α and β, which allows docking at the cytoplasmic side of the nuclear pore [E. J. Tran, S. R. Wente, Cell 125, 1041 (Jun. 16, 2006)]. Movement through the nuclear pore is regulated by the small GTPase Ran, which in its GTP-bound state promotes the dissociation of the imported protein from the importins and their recycling back to the cytoplasm [J. Moroianu, J Cell Biochem Suppl 32-33, 76 (1999)].

However, not all cyto-nuclear shuttling proteins contain the canonical NLS, and therefore use other, NLS-independent, mechanisms for their passage through the NPC. Some of the characterized NLS-independent mechanisms include passive diffusion of small proteins (<30-40 kDa), distinct nuclear-directing motifs [D. Christophe, C. Christophe-Hobertus, B. Pichon, Cell Signal 12, 337 (May 2000)], interaction with NLS-containing proteins, or alternatively, a direct interaction with the nuclear pore proteins (NUPs); [L. Xu, J. Massague, Nat Rev Mol Cell Biol 5, 209 (March 2004)]. However, the kinetics of shuttling and nuclear retention by these mechanisms are usually too slow to allow timely transient transcription, and therefore the molecular mechanism(s) that allows the rapid and reversible NLS-independent translocation of signaling proteins upon stimulation is still obscure.

Chuderland et al, 2008, Mol Cell 31, 850-861 and Plotnikov et al., 2011, Mol Cell Biol 31, 3515-3530 teach that ERK1/2 translocation involves CK2-mediated phosphorylation of two Ser residues within a nuclear translocation signal (NTS) of ERK1/2. This phosphorylation allows interaction with Imp7, which further facilitates ERK1/2 shuttling via nuclear pores.

The ability to regulate the cellular localization of a biological component is important for many functions such as the regulation of nucleic acid expression, transfection of eukaryotic cells, gene therapy, protection from toxic chemicals and transport of anti-cancer agents. There is thus a widely recognized need for, and it would be highly advantageous to identify novel sequences capable of regulating nuclear translocation.

Additional background art includes U.S. Patent Application No. 20100099627.

SUMMARY OF THE INVENTION

According to an aspect of some embodiments of the present invention there is provided an isolated peptide comprising an amino acid sequence being at least 80% homologous to the sequence as set forth in SEQ ID NO: 1 (PERYQNLSPV), the isolated peptide comprising a nuclear targeting activity, the peptide being no longer than 20 amino acids.

According to an aspect of some embodiments of the present invention there is provided an isolated peptide comprising an amino acid sequence being at least 80% homologous to the sequence as set forth in SEQ ID NO: 1 (PERYQNLSPV), the isolated peptide being capable of preventing the isolated peptide being capable of preventing P38α nuclear translocation, the peptide being no longer than 20 amino acids.

According to an aspect of some embodiments of the present invention there is provided a method of treating an inflammatory or immune disorder in a subject, the method comprising administering to the subject a therapeutically effective amount of the isolated peptide described herein into the subject, thereby treating the inflammatory or immune disease.

According to an aspect of some embodiments of the present invention there is provided a composition of matter comprising the isolated peptide described herein and a heterologous substance linked to the amino acid sequence via a linker.

According to an aspect of some embodiments of the present invention there is provided an isolated polynucleotide comprising a nucleic acid sequence encoding the peptide described herein.

According to an aspect of some embodiments of the present invention there is provided a nucleic acid construct comprising the isolated polynucleotide described herein.

According to an aspect of some embodiments of the present invention there is provided a method of targeting a substance into a nucleus of a host cell, the method comprising introducing the substance into the host cell, the substance being attached to the peptide described herein.

According to an aspect of some embodiments of the present invention there is provided a method of targeting a substance into a nucleus of a host cell, the method comprising introducing the peptide described herein into the host cell, the peptide being linked to an affinity moiety capable of binding the substance.

According to an aspect of some embodiments of the present invention there is provided an isolated cell comprising the nucleic acid construct described herein.

According to an aspect of some embodiments of the present invention there is provided a pharmaceutical composition comprising as an active agent the peptide described herein and a pharmaceutically acceptable carrier.

According to some embodiments of the invention, the peptide comprises the sequence as set forth in SEQ ID NO: 1 or SEQ ID NO: 8.

According to some embodiments of the invention, at least one of the amino acids is a synthetic amino acid.

According to some embodiments of the invention, at least one of the amino acids is a D stereoisomer.

According to some embodiments of the invention, at least one of the amino acids is an L stereoisomer.

According to some embodiments of the invention, a heterologous substance is linked to the amino acid sequence via a linker.

According to some embodiments of the invention, the isolated peptide of comprises the amino acid sequence as selected from the group consisting of SEQ ID NO: 2 (PERYQNLSPVG), SEQ ID NO: 3 (PERYQNLSPVGS), SEQ ID NO: 4 (PERYQNLSPVGSG), SEQ ID NO: 5 (PERYQNLSPVGSGA) SEQ ID NO: 6 (KPERYQNLSPVGSGA) and SEQ ID NO: 7 (KPERYQNLSPVAAAA).

According to some embodiments of the invention, the isolated peptide comprises the sequence at least 80% homologous to the sequence as set forth in SEQ ID NO: 8 (KPERYQNLSPV).

According to some embodiments of the invention, the isolated peptide is myristoylated.

According to some embodiments of the invention, the immune disorder is an autoimmune disorder.

According to some embodiments of the invention, the inflammatory disease is colitis.

According to some embodiments of the invention, the peptide is for use in treating an inflammatory or immune disorder.

According to some embodiments of the invention, the heterologous substance is selected from the group consisting of a polypeptide, a nucleic acid, a small molecule and a carbohydrate.

According to some embodiments of the invention, the heterologous substance is a polypeptide.

According to some embodiments of the invention, the heterologous substance is a pharmaceutical agent.

According to some embodiments of the invention, the pharmaceutical agent is a therapeutic agent, a cosmetic agent or a diagnostic agent.

According to some embodiments of the invention, the composition is linked to a detectable moiety via a linker.

According to some embodiments of the invention, the linker comprises a peptide bond.

According to some embodiments of the invention, the linker comprises a non-peptide bond.

According to some embodiments of the invention, the composition of matter is linked to an affinity moiety via a linker.

According to some embodiments of the invention, the affinity moiety is selected from the group consisting of an antibody, a receptor ligand and a carbohydrate.

According to some embodiments of the invention, the construct further comprises a cis regulatory element for regulating expression of the polynucleotide.

According to some embodiments of the invention, the isolated polynucleotide is transcriptionally fused to a nucleic acid sequence encoding a heterologous polypeptide sequence of interest.

According to some embodiments of the invention, the isolated cell is eukaryotic.

According to some embodiments of the invention, the eukaryotic cell is a yeast cell.

According to some embodiments of the invention, the substance is an endogenous substance.

According to some embodiments of the invention, the substance is an exogenous substance.

According to some embodiments of the invention, the method further comprises administering the exogenous substance into the host cell prior to, concomitant with or following the introducing.

According to some embodiments of the invention, the host cell is a dividing cell.

According to some embodiments of the invention, the host cell is a non-dividing cell.

According to some embodiments of the invention, the substance is selected from the group consisting of a polypeptide, a nucleic acid, a small molecule and a carbohydrate.

According to some embodiments of the invention, the substance is a nucleic acid.

According to some embodiments of the invention, the nucleic acid is introduced into the host cell by a method selected from the group consisting of: microinjection, electroporation, calcium phosphate coprecipitation, DEAE dextran introduction, liposome mediated introduction, viral mediated introduction, naked DNA injection, and biolistic bombardment.

According to some embodiments of the invention, the targeting is effected in vivo.

According to some embodiments of the invention, the targeting is effected ex vivo.

According to some embodiments of the invention, the targeting is effected in vitro.

According to some embodiments of the invention, the host cell is a eukaryotic cell.

According to some embodiments of the invention, the eukaryotic cell is a yeast cell.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
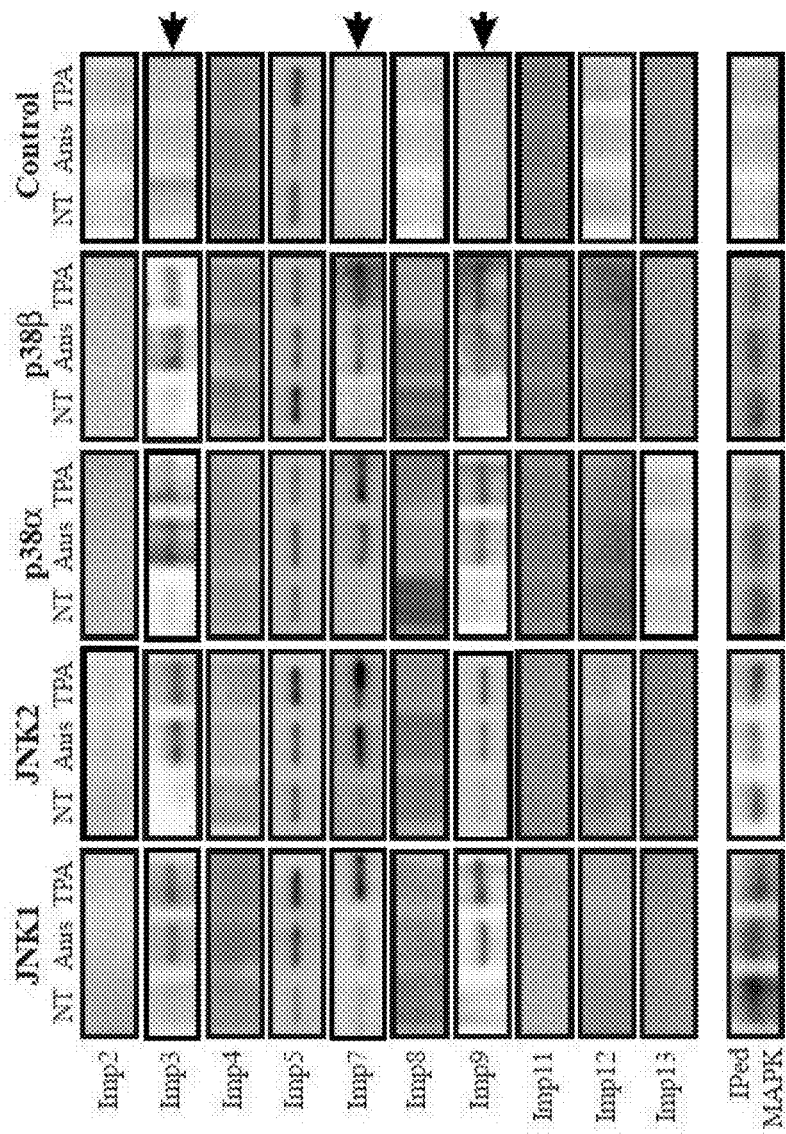
Figure 1B:
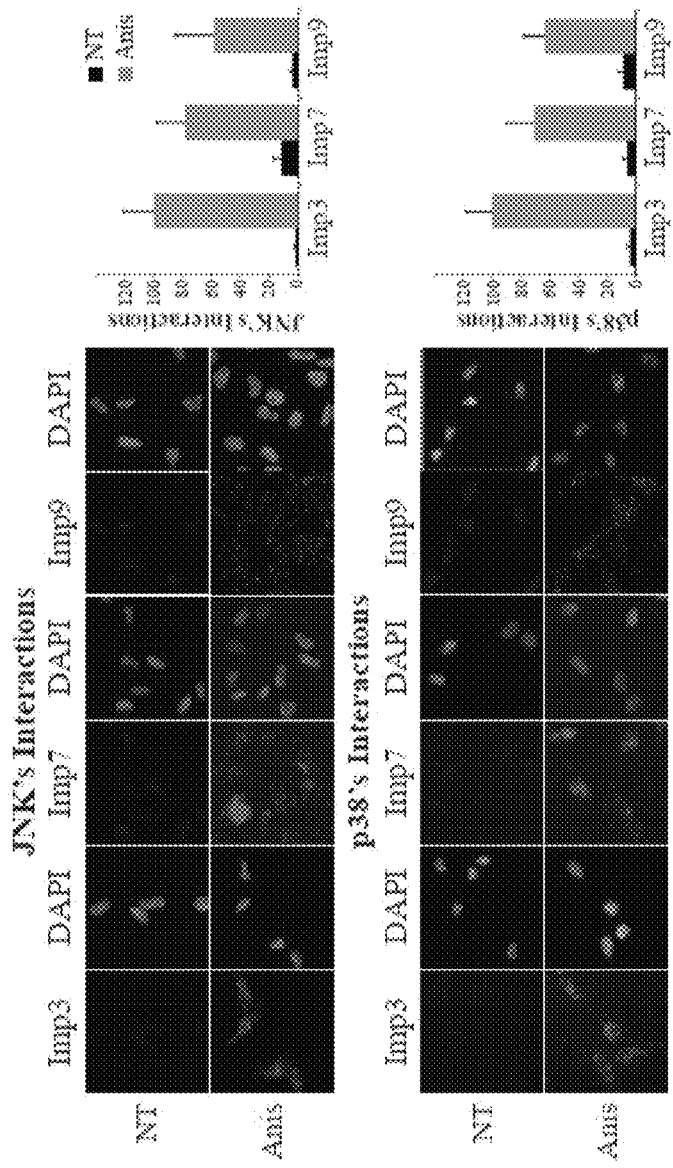

FIGS. 1A-1B illustrate that JNK1/2 and p38α/β interact with Imp3, 7 and 9 in HeLa cells. (A) Co-IP studies. HeLa cells were grown to 70% confluence, serum starved (0.1% FBS, 16 hrs), and then either stimulated with Anisomycin (Anis; 0.5 µg/ml, 15 min) and TPA (250 nM, 15 min), or left untreated (NT). Cell extracts were then subjected to Co-IP with anti JNK1, JNK2, p38α, p38β Abs, or rabbit IgG as a negative control (Control). The interacting Imps were detected by Western blot with the indicated anti Imps Abs. Amount of IPed MAPKs was detected by the anti JNK1, JNK2, p38α and p38β Abs or IgG control as indicated (bottom panels). The blots were developed with either NBT/BCIP or ECL. Arrows indicate the interacting Imps. (B) Studies using PLA. HeLa cells were grown on slides to 70% confluence, serum starved, and then were either stimulated with Anisomycin (Anis), or left untreated (NT). Cells were fixed, and subjected to a PLA assay according to the manufacturer's instructions using the anti Imps Abs together with either anti JNK (upper panel) or anti p38 (lower panel) as indicated. The nuclei were detected using DAPI, and slides were visualized using a fluorescent microscope. Quantification of the intensity of the signal was performed using ImageJ analysis tool (data shown represents mean±S.E. p<0.0001 (treated Vs. control)).

Figure 2C:
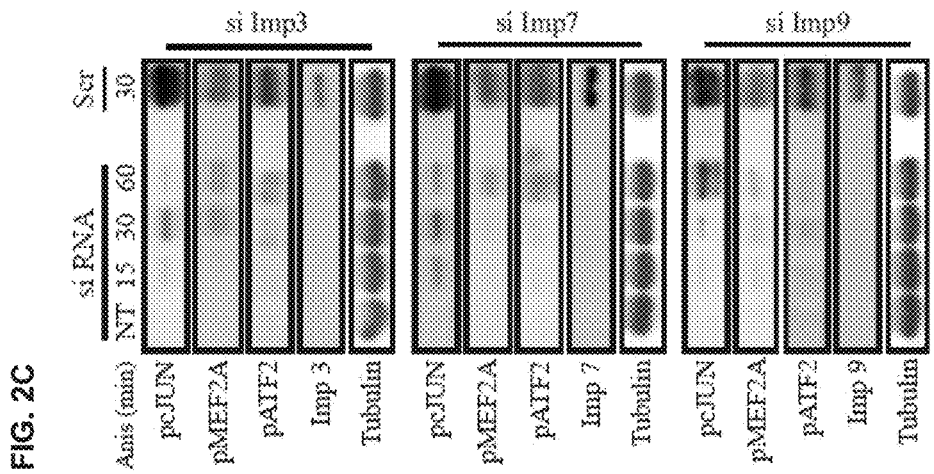
Figure 2B:
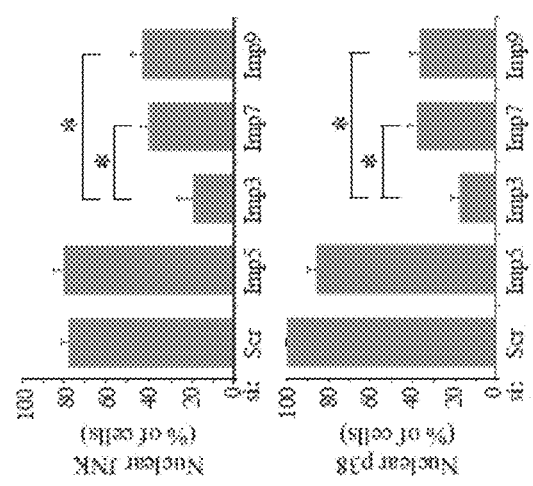

FIGS. 2A-2C illustrate that Imp3, 7 and 9 are required for JNK and p38 translocation and induced transcription. (A) Si RNAs of Imp3, 7, 9, but not Imp5, inhibit the stimulated JNK and p38 nuclear translocation. HeLa cells were grown on cover slides to 30% confluence. si RNAs of the indicated Imps and si Control supplied by the company (si Scr, negative control) were then transfected to the cells using Dharmafect according to the manufacturer's instructions. Forty eight hrs after transfection, the cells were serum starved, then either stimulated with Anisomycin (0.5 µg/ml, 15 min), or left untreated (NT) as indicated. The cells were then fixed, stained using the indicated (left) anti MAPK Abs and visualized using a fluorescent microscope. (B) Quantification of JNKs/p38s nuclear localization prior and upon stimulation. Data shown represents mean±S.E. The significance of Imp3 vs. Imp7/Imp9 (*) was p<0.0003. The significance of stimulated Imp3/7/9 vs Scr was p<0.00001 (C) Si RNA of Imp3, 7, 9 inhibit the activation of downstream transcription factor targets of JNKs/p38s. HeLa cells were transfected with si RNAs of the indicated Imps and si control supplied by the manufacturer (si Scr, negative control) using Dharmafect according to the manufacturer instructions. Forty eight hrs after transfection, the cells were serum starved, and then stimulated with Anisomycin (Anis 0.5 µg/ml) for the indicated times or left untreated (NT). Cell extracts were subjected to a Western blot analysis with anti pJUN, pMEF2A, pATF2, indicated Imps, and tubulin Abs.

Figure 3A:
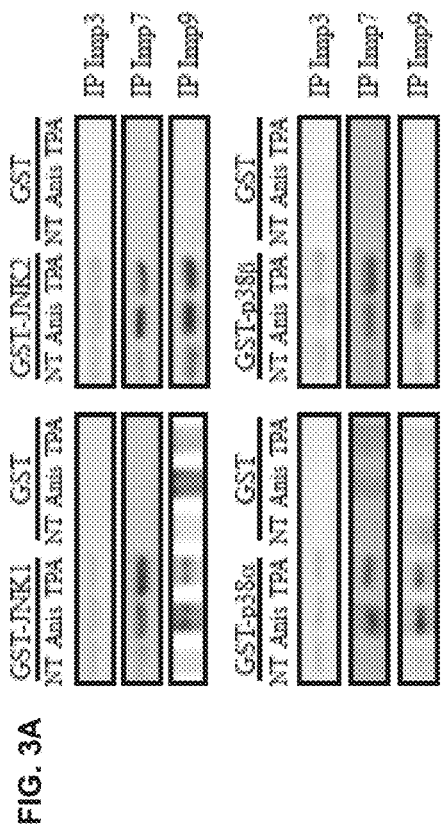
Figure 3B:
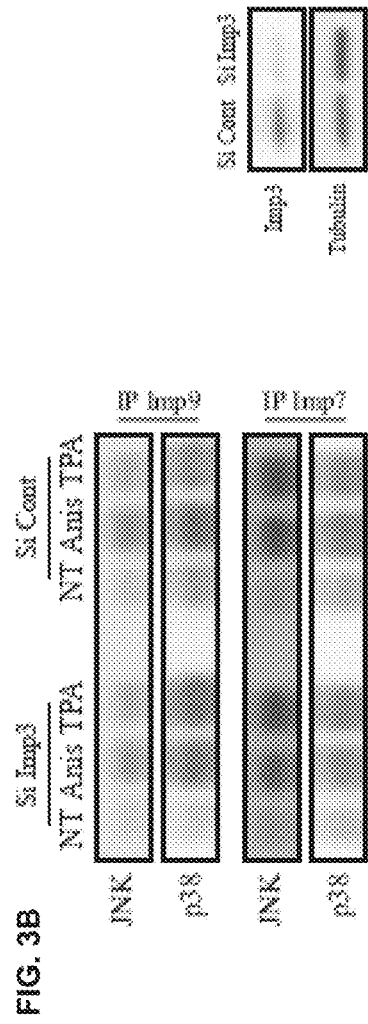

FIGS. 3A-3B illustrate that JNK1/2 and p38α/β directly interact with either Imp7 or Imp9 but not with Imp3. (A) In vitro interaction of JNK1/2 and p38α/β with Imp3/7/9. Purified Imp3/7/9 were prepared by IP as follows: HeLa cells were grown to 70% confluence, serum starved, and then were either stimulated with Anisomycin (Anis 0.5 µg/ml, 15 min), TPA (250 nM, 15 min) or left untreated (NT). Imp3/7/9 were then IPed from the cell's extracts and extensively washed, twice with RIPA buffer and once with 0.5M LiCl. The indicated GST-MAPKs were prepared from bacteria as described under Materials and methods. To examine association, 500 ng of each GST-MAPK were incubated with 20 µl of the indicated IPed Imps in PBS (2 hrs, 4° C., with rotation). The beads were then washed with washing buffer containing 150 mM NaCl, and interacting MAPKs were detected using Western blot analysis with the indicated Abs. (B) Imp3 is not required for Imp7/9 interactions with JNK1/2 and p38α/β. HeLa cells were treated with Si RNAs of Imp3 according to the manufacturer instructions. Forty eight hrs after transfection, the cells were serum starved, and then stimulated with Anisomycin (Anis 0.5 µg/ml) or TPA (TPA 250 ng) or left untreated (NT). Cell extracts were then subjected to Co-IP with anti Imp7 or Imp9, the interacting MAPKs were detected by Western blot with the indicated Abs. Amount of IPed Imps was detected by the indicated Abs.

Figure 4A:
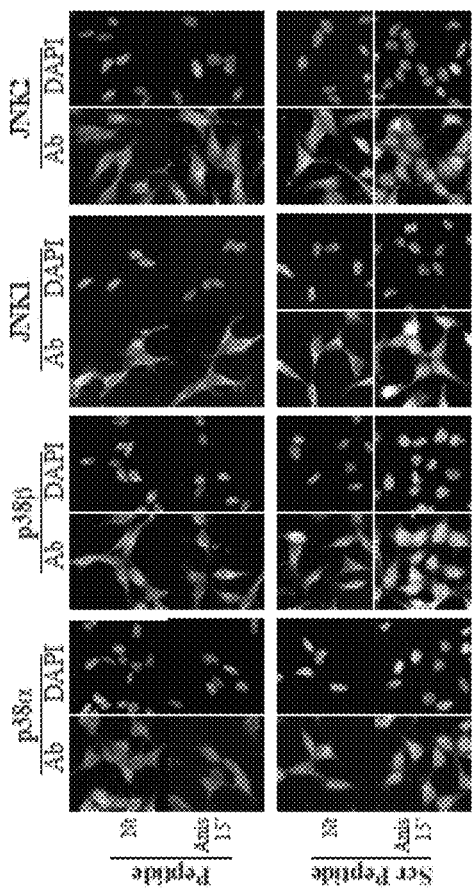
Figure 4B:
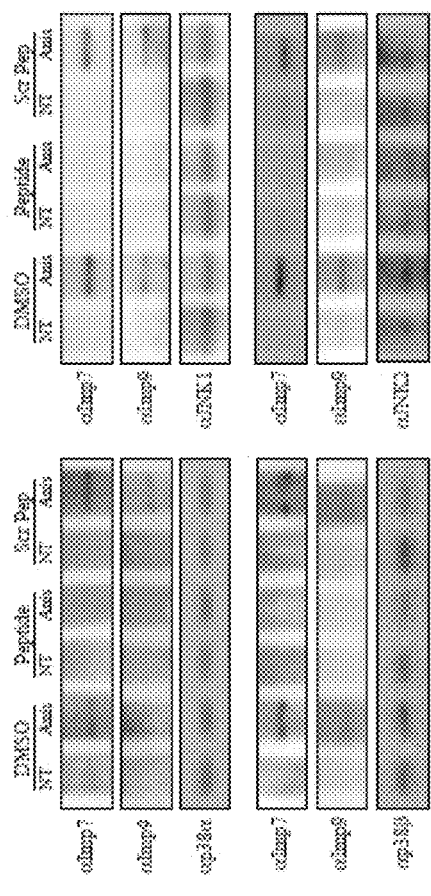

FIGS. 4A-4B illustrate that a myristoilated peptide derived from amino acids 21-33 of p38α inhibits the stimuli-dependent nuclear translocation and interaction of JNK1/2 and p38α/β with Imp7. (A) The peptide inhibits the stimuli-dependent nuclear translocation of JNK1/2 and p38α/β. HeLa cells were grown on slides to 70% confluence, serum starved (0.1% FBS, 16 hrs), and then either incubated with the inhibitory peptide (Peptide, 10 µM) or scrambled peptide (Scr peptide, 10 µM), cells were then treat with Anisomycin (Anis, 0.5 µg/ml) or left untreated (NT). Cells were fixed, and stained with anti JNK1, JNK2, p38α or p38β Abs as indicated, and DAPI to detect nuclei. The slides were visualized using a fluorescent microscope. (B) The peptide inhibits the interaction of JNK1/2 and p38α/β with Imp7. HeLa cells were grown to 70% confluence, serum starved (0.1% FBS, 16 hrs), and then either incubated with the inhibitory peptide (Peptide, 10 µM), scrambled peptide (Scr peptide, 10 µM), or DMSO, followed by treatment with Anisomycin (Anis, 0.5 µg/ml) or mock control (NT). Cell extracts were then subjected to Co-IP with anti JNK1, JNK2, p38α, p38β Abs. The interacting Imp7 was detected by Western blot with the indicated anti Imps Abs. Amount of IPed MAPKs was detected by the anti JNK1, JNK2, p38α and p38β Abs as indicated.

FIGS. 5A-5D illustrate that Imp3 interacts with Imp7/9-MAPK dimer in a phospho-dependent manner (A) Detecting heterodimerization of Imp3/7/9 using PLA. HeLa cells were grown on slides to 70% confluence, serum starved, and stimulated with Anisomycin (Anis, 0.5 µg/ml 15 min). Thereafter, the cells were fixed and subjected to a PLA, using the Abs indicated on top. The nuclei were detected using DAPI, and slides were visualized using a fluorescent microscope. (B) Quantification of the intensity of the signal was performed using ImageJ analysis tool. Data shown represents mean±S.E. The significance of stimulated vs NT was p<0.0005. (C) Detecting Imp3/7/9 interaction by CoIP. Serum-starved HeLa cells (0.1% FBS, 16 hrs) were treated with Anisomycin (Anis 0.5 µg/ml) or TPA (250 nM) for 15 min. Cell extracts were then subjected to a Co-IP with the Abs indicated on right. The blots of the CoIPs and IPed Imps (bottom panels) were developed with the Abs indicated on the left with either NBT/BCIP or ECL. (D) The interaction of Imp3 to Imp7/9 is dependent on Imp3 phosphorylation. Purified Imp3 was prepared by IP as follows: HeLa cells were grown on to 70% confluence, serum starved, and then were either stimulated with TPA (250 nM, 15 min) or left untreated (NT). Imp3 was then IPed from the cell's extracts and extensively washed, twice with RIPA buffer and once with 0.5M LiCl. Then the purified protein was either incubated with Calf Intestinal phosphatase, (CIP, 1 hrs, 37° C.) or left untreated. 500 ng of the indicated recombinant Imps were incubated with the IPed Imp3 (2 hrs, 4° C., with rotation). The beads were then washed with a washing buffer containing 150 mM NaCl, and interacting Imps were detected using Western blot analysis with the indicated Abs.

Figure 6A:
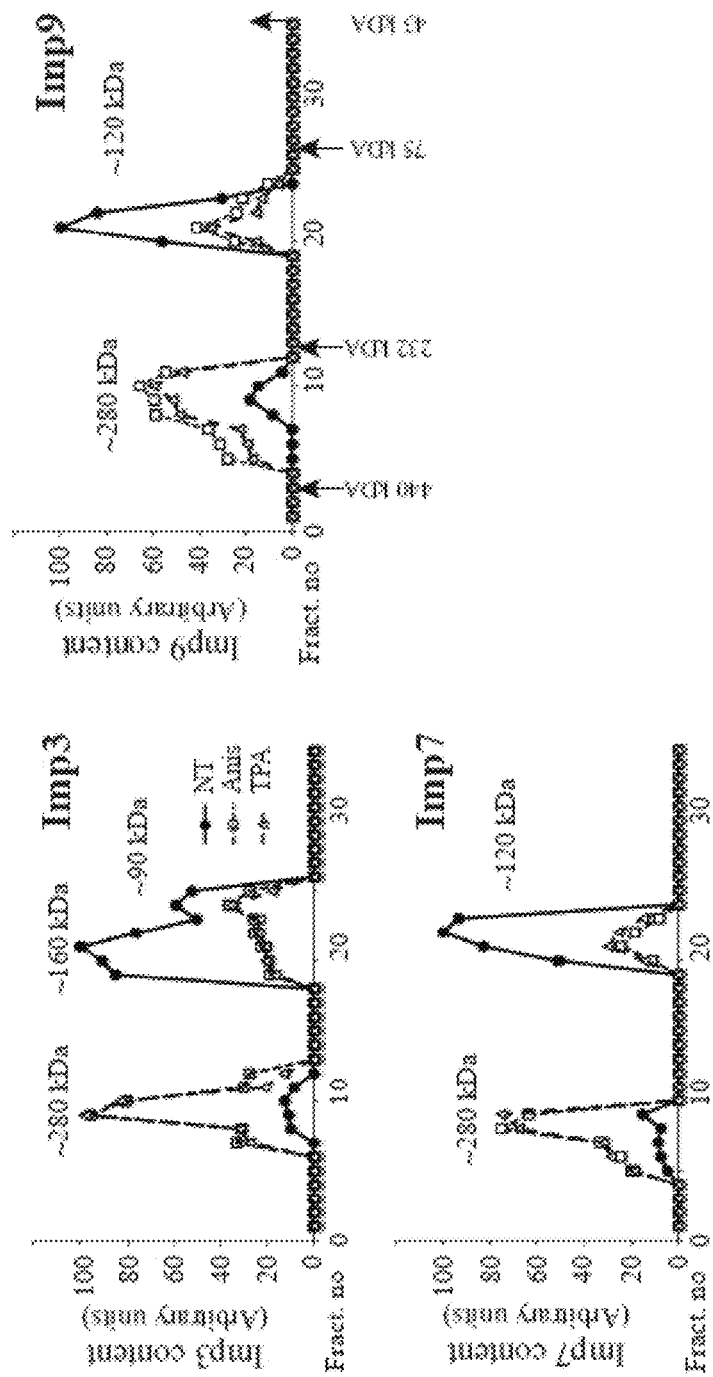

FIGS. 6A-6B illustrate that p38 and JNK form complexes with dimers of either Imp3/7 or Imp3/9 after stimulation. (A) Gel filtration studies reveal MW shift of Imp3/7/9 upon stimulation. HeLa cells were serum starved and then were either stimulated with Anisomycin (Anis, 0.5 µg/ml, 15 min) and TPA (250 nM, 15 min), or left untreated (NT). Cell extracts (20 mg of each treatment) were loaded on a 16/60 superdex 200 sizing column (rate of 1 ml/min), and 1 ml fractions were collected. The fractions were then analyzed using Western blot with the anti Imp3/7/9 Abs indicated on left. (B) CoIP confirms association of JNK and p38 with Imp dimers in the ~280 kDa but not the ~120 kDa peaks. Fractions representing the ~280 kDa and ~120 kDa peaks (fractions no. 9 and 22), from each of the non-treated, Anis or TPA stimulated columns, were subjected to CoIP with the indicated (right) Abs. The interacting proteins were detected using Western blot analysis with the indicated (left) Abs.

Figure 7A:
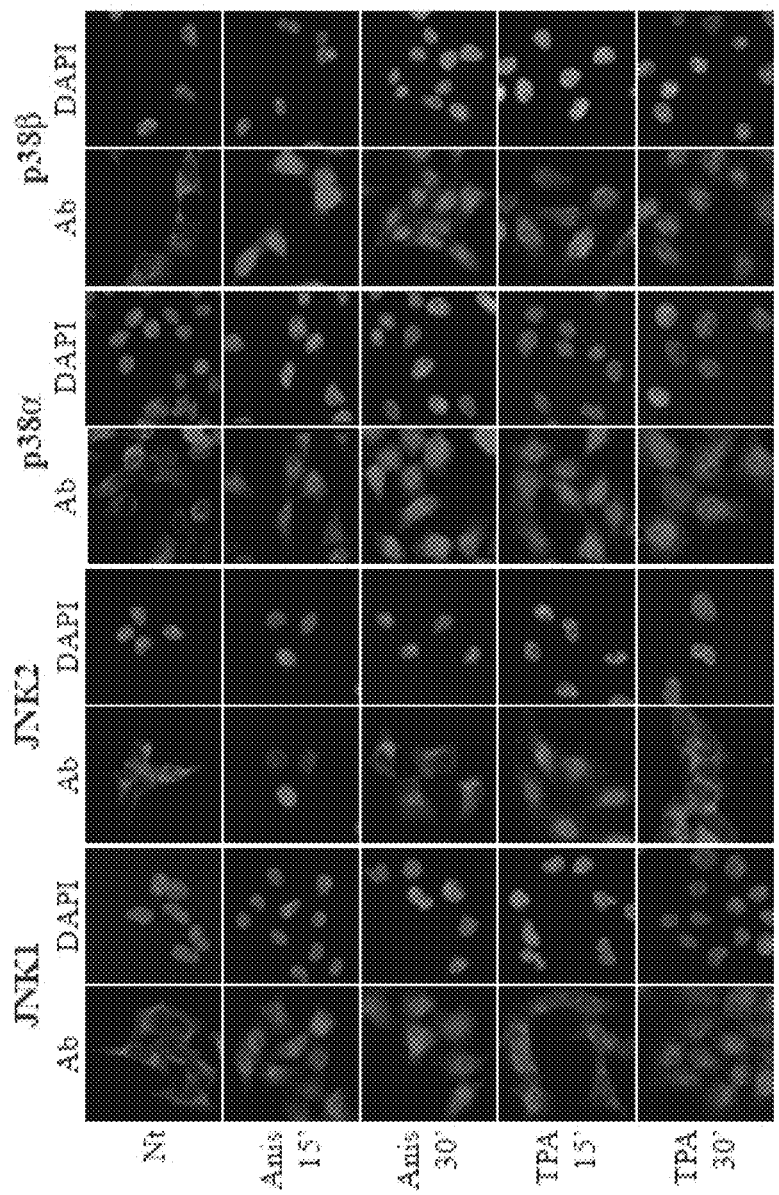

FIGS. 7A-7B illustrate that JNK1/2 and p38α/β translocate into the nucleus independently of their activatory phosphorylation. (A) Nuclear translocation of JNK1/2 and p38α/β. HeLa cells were grown on slides to 70% confluence, serum starved (0.1% FBS, 16 hrs), and then either stimulated with Anisomycin (Anis, 0.5 µg/ml) and TPA (250 nM) for the indicated time points, or left untreated (NT). Cells were fixed, and stained with anti JNK1, JNK2, p38α or p38β Abs as indicated, and DAPI to detect nuclei. The slides were visualized using a fluorescent microscope (Olympus BX51, ×40 magnification). (B) The nuclear translocation of endogenous JNK1/2 and p38α/β is independent of their phosphorylation. HeLa cells were grown to 70% confluence, serum starved, and then stimulated with Anisomycin (0.5 µg/ml) or TPA (250 nM) for the indicated time points. Cell extracts were produced and subjected to Western blot analysis with the indicated Abs. The blots were developed with either NBT/BCIP or ECL.

FIGS. 8A-8B illustrate that JNK1/2 and p38α/β translocate into the nucleus in MCF10A and HB2 cells. (A, B) Nuclear translocation of JNK1/2 and p38α/β in MCF10A and HB2 cells. (A) HB2 and (B) MCF10A cells were grown on slides to 70% confluence, serum starved and stimulated with Anisomycin (Anis, 0.5 µg/ml) or TPA (250 nM, only for HB2). Cells were fixed, and stained using anti JNK and p38 Abs as indicated on top. The nuclei were detected using DAPI, and the slides were visualized using a fluorescent microscope (Olympus BX51, ×40 magnification).

Figure 9:
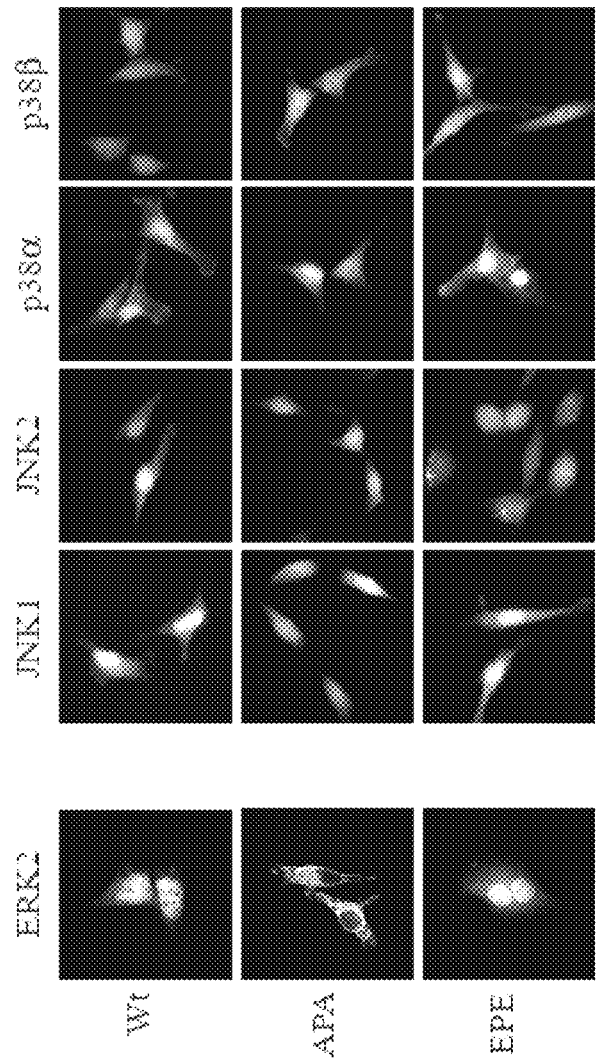

FIG. 9 illustrates that JNK1/2 and p38α/β translocate into the nucleus using NTS-independent mechanism. Mutations in the NTS-homologous region do not affect the nuclear shuttling of JNK1/2 and p38α/β. HeLa cells were grown on slides to 70% confluence, transfected with JNK1-GFP (wt-JNK1), JNK2-GFP (wt-JNK2), p38α-GFP (wt-p38α) or p38β-GFP (wt-p38β) and their mutants (APA or EPE). Sixteen hrs after transfection the cells were serum starved, fixed, and visualized using a fluorescent microscope (Olympus BX51, ×40 magnification).

Figure 10A:
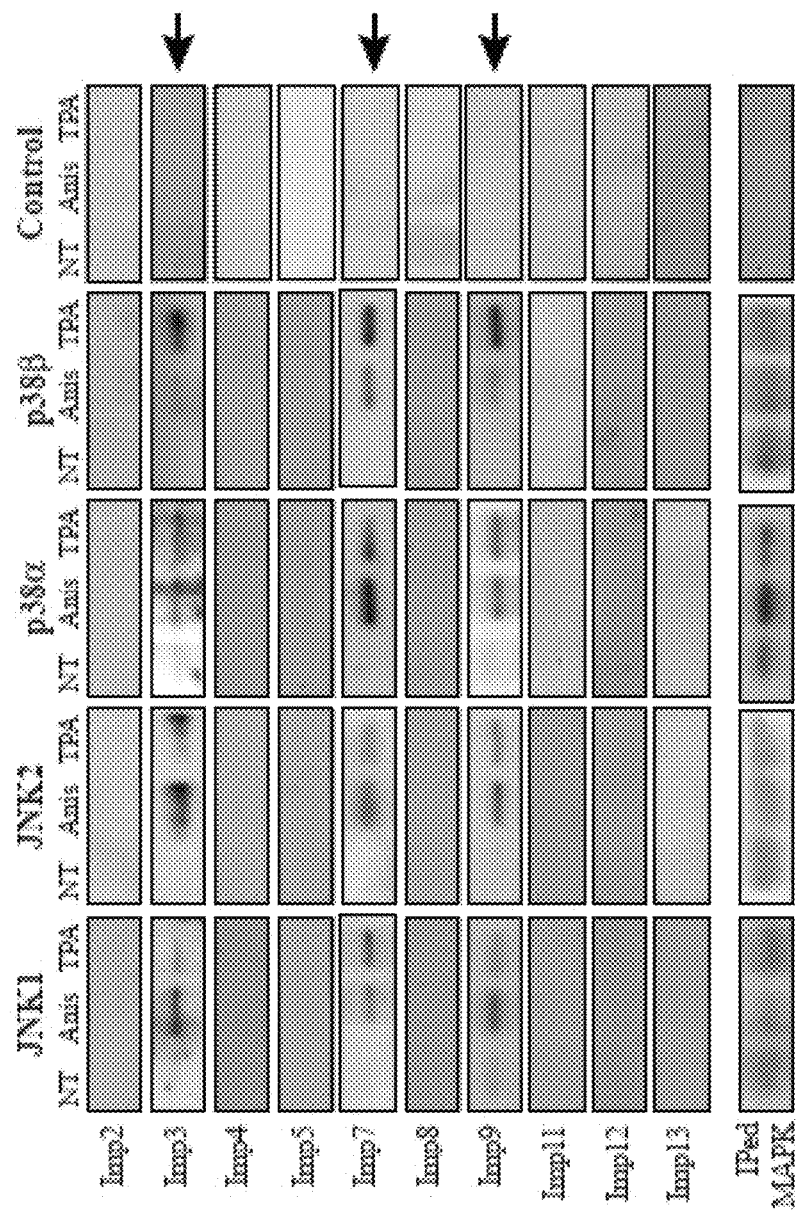
Figure 10B:
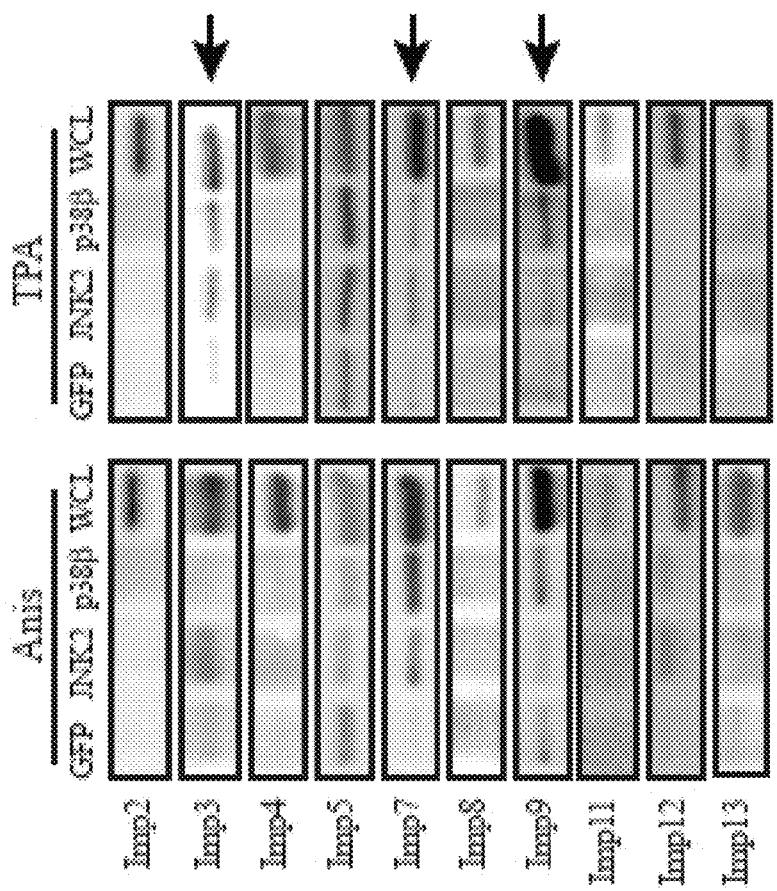

FIGS. 10A-10B illustrate that endogenous and overexpressed JNK1/2 and p38α/β CoIP with Imp3, 7 and 9. (A) A Co-IP screen to detect the importins interacting with JNK1/2 and p38α/β in MCF7 cells. MCF7 cells were grown on slides to 70% confluence, serums starved and then were either stimulated with Anisomycin (Anis 0.5 µg/ml, 15 min), TPA (250 nM, 15 min) or left untreated (NT). Cells extracts were then subjected to Co-IP with anti JNK1, JNK2, p38α, or p38β, and rabbit IgG as a negative control (Control). The interacting Imps or the IPed MAPKs were detected by Western blot with the indicated Imps or MAPK Abs. (B) Interaction of overexpressed MAPKs in HeLa cells. HeLa cells were transfected with either JNK2-GFP (wt-JNK2), p38ββ-GFP (wt-p38β) or GFP alone. Cells were serum starved, and then treated with Anisomycin (Anis 0.5 µg/ml, 15 min), TPA (250 nM, 15 min). Cells extracts were then subjected to a CoIP with anti GFP Abs. The interacting Imps and the loading extracts were detected using Western blot analysis with the indicated (left) Abs. The blots were developed with either NBT/BCIP or ECL. Arrows indicate interacting Imps.

Figure 11:
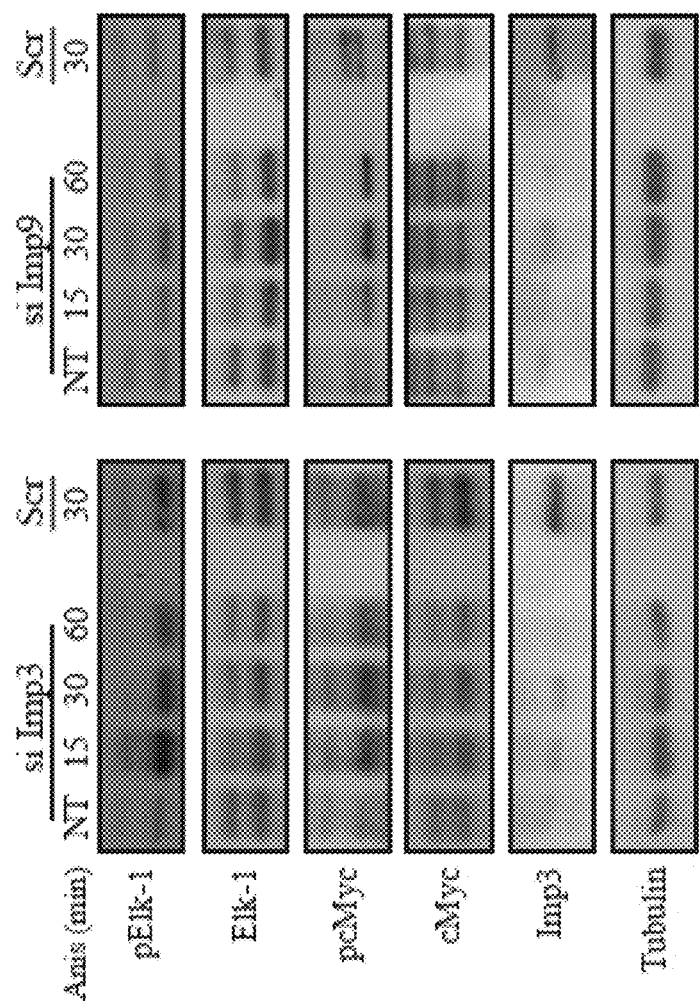

FIG. 11 illustrates that knockdown of Imp3/9 did not effect on the phosphorylation of ERK substrate cMyc. Si RNA of Imp3, 9 did not inhibit the activation of downstream transcription factor targets of ERK1/2. HeLa cells were transfected with si RNAs of the indicated Imps and si control supplied by the manufacturer (si Scr, negative control) using Dharmafect according to the manufacturer instructions. Forty eight hrs after transfection, the cells were serum starved, and then stimulated with Anisomycin (Anis 0.5 µg/ml) for the indicated time points or left untreated (NT). Cell extracts were subjected to a Western blot analysis with the indicated Abs, the blots were developed with either NBT/BCIP or ECL.

Figure 12A:
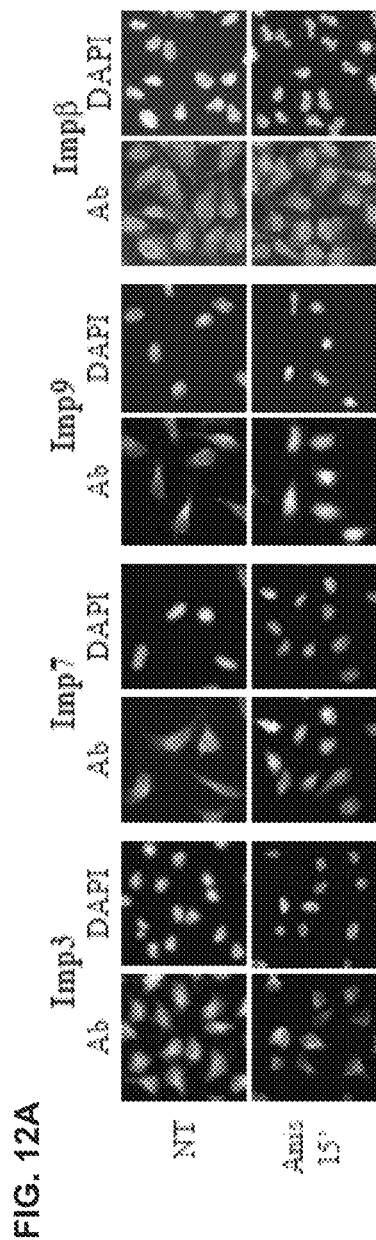
Figure 12B:
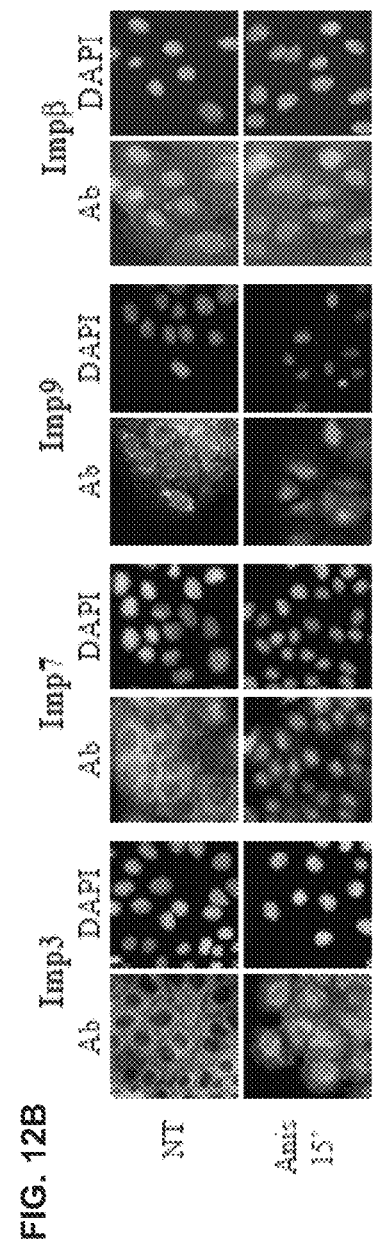

FIGS. 12A-12B illustrate Imp3/7/9 translocation in response to stimuli. HeLa (A) or HB2 (B) cells were grown on slides to 70% confluence, serum starved, and then either stimulated with Anisomycin (Anis 0.5 m/ml 15 min) or left untreated (NT). Cells were fixed and stained using the indicated Abs. The nuclei were detected using DAPI and slides were visualized using a fluorescent microscope (Olympus BX51, ×40 magnification).

Figure 13:
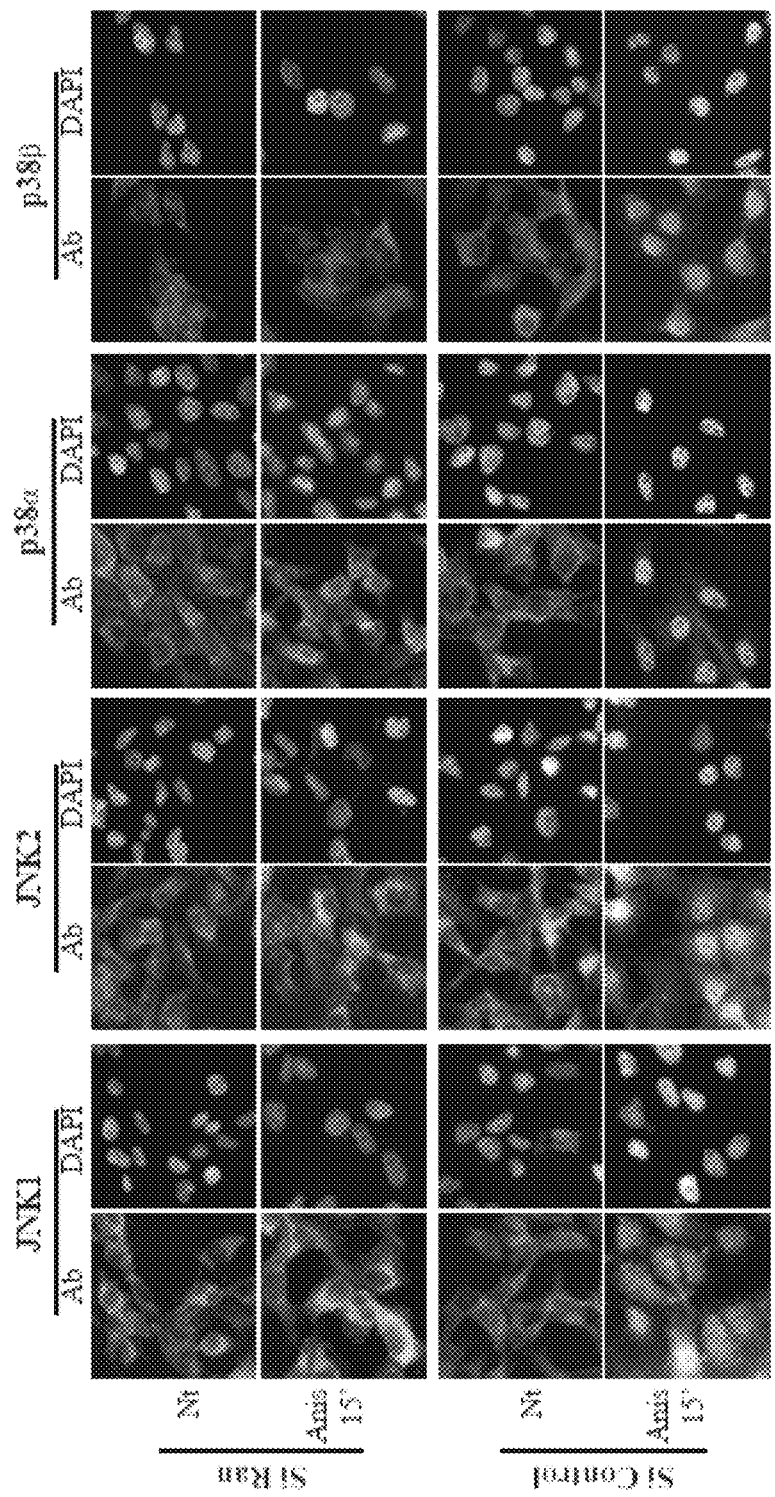

FIG. 13 illustrates that Ran is required for JNK1/2 and p38α/β nuclear translocation. siRNAs of Ran inhibits the stimuli-dependent JNK1/2 and p38α/β nuclear translocation. HeLa cells were grown on cover slides to 30% confluence. siRNA Ran and si Control supplied by the company (si Scr, negative control) were then transfected to the cells using Dharmafect according to the manufacturer's instructions. Forty eight hrs after transfection, the cells were serum starved, then either stimulated with Anisomycin (0.5 µg/ml, 15 min), or left untreated (NT) as indicated. The cells were then fixed, stained using the indicated anti MAPK Abs and visualized using a fluorescent microscope (Olympus BX51, ×40 magnification).

FIGS. 14A-14C illustrate identification of p38α interaction site with Importin7. (A) schematic representation of the truncation mutation of p38α. (B) Deletion mutation to the N terminal of p38 a inhibits its nuclear translocation. ΔC (40a.a) or ΔN (20 or 30a.a) terminus deletion mutations of p38α-GFP were constructed and transfected to HeLa cells. Sixteen hrs after transfection the cells were serum starved, either stimulated with Anisomycin (0.5 µg/ml, 15 min), or left untreated (NT). Cells were fixed, the nuclei were detected using DAPI and slides were visualized using a fluorescent microscope (Olympus BX51, ×40 magnification). (C) Deletion mutation to the N terminal of p38α inhibits its interaction with Imp7/9. Consecutive deletion mutation of the N-terminus of p38α-GFP were constructed and transfected to HeLa cells. Sixteen hrs after transfection the cells were serum starved, either stimulated with Anisomycin (0.5 µg/ml, 15 min), or left untreated (NT). Cells extracts were then subjected to a CoIP with anti GFP Abs. The interacting Imp7 and the loading extracts were detected using Western blot analysis with the indicated (left) Abs. The blots were developed with either NBT/BCIP or ECL. Arrows indicate interacting Imps.

FIGS. 15A-15B illustrate that JNK (FIG. 15A) and p38 (FIG. 15B) MAPKs form complexes upon stimulation. HeLa cells were serum starved and then either stimulated with Anisomycin (Anis, 0.5 µg/ml, 15 min), TPA (250 nM, 15 min) or left untreated (NT). Cell extracts were loaded on a 16/60 superdex 200 sizing column (flow rate 1 ml/min), and 1 ml fractions were collected. The fractions were then analyzed, using Western blot with the anti JNK/p38 Abs, as indicated. The blots were developed with either NBT/BCIP or ECL.

Figure 16:
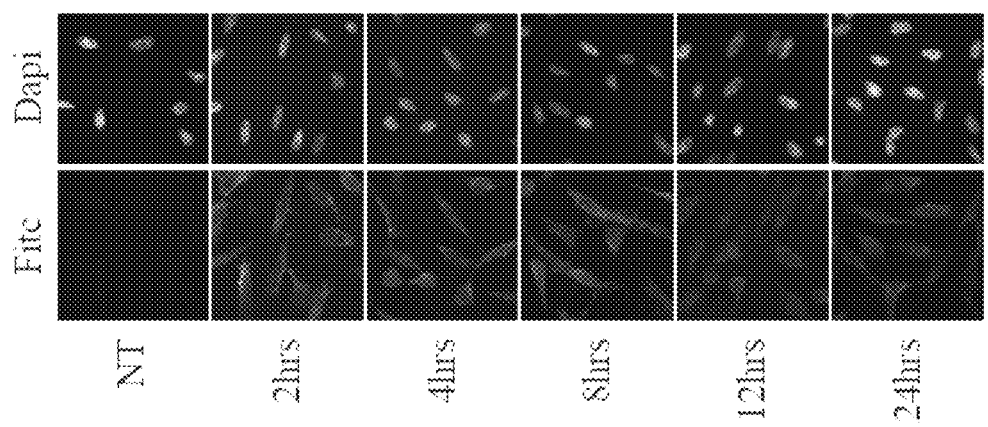

FIG. 16 illustrates the intracellular distribution and stability of myristoylated Peptide. HeLa cells were grown on cover slips to 70% confluence, serum starved (0.1% FBS, 16 hrs), and treated peptide conjugated with myristic acid on its N-term and biotin on its C-term for the indicated times. Cells were fixed with 3% PFA and stained with Avidin-FITC and DAPI. The peptide was visualized using a fluorescent microscope (×40 magnification).

FIGS. 17A-17C illustrate the use of inhibitory peptide as a potential therapeutic agent in colitis model. 21 male C57BL mice treated (I.V every 48 hours) with either peptide (15 mg/Kilo), scramble peptide (15 mg/Kilo) or DMSO (2%). Colitis was induced using DSS (1.25% in drinking water) and mice were sacrificed 7 days post induction. (A-C). Colitis was evaluated using endoscopic imaging and scored for the number of lesions in the colon and weight of mice.

Figure 18B:
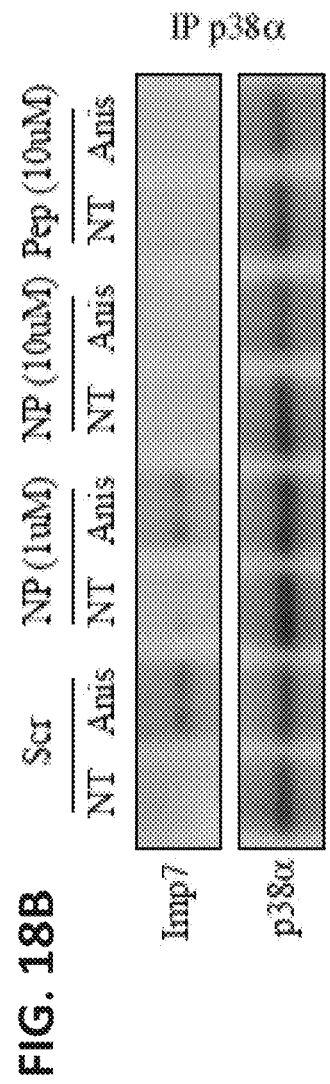

FIGS. 18A-18B illustrate that myristiolated peptide blocks the interaction of p38 with Importin 7. (A) Myristiolated peptide was modified (replacement of 3 residues to alanin) Myr-KPERYQNLSPVGSGA—SEQ ID NO: 9; Myr-KPERYQNLSPVAAAA—SEQ ID NO: 10. (B) Hela cells were pre-incubated with modified peptide (2 hours) then either stimulated with anisomycin (Anis, 0.5 µg/ml, 15 min) or left untreated. Cell extracts were then subjected to CoIP with anti p38a. The interacting Imp7 or IPed p38 were detected by Western blot with indicated Abs.

FIGS. 19A-19C illustrate that myristoylated peptides inhibit the stimulation dependent nuclear translocation of p38. HeLa cells were grown on slides to 70% confluence, serum starved and pre-incubated with either new peptide (NP), peptide or scrambled peptide and then either stimulated with Anisomycin (Anis 0.5 µg/ml 15 min) or left untreated (NT). Cells were fixed and stained using the indicated Abs. The nuclei were detected using DAPI and slides were visualized using a spinning disc confocal microscope (Zeiss, ×100 magnification).

FIGS. 20A-20C illustrate that myristoylated peptides inhibit the stimulation dependent nuclear translocation of JNK. HeLa cells were grown on slides to 70% confluence, serum starved and pre-incubated with either new peptide (NP), peptide or scrambled peptide and then either stimulated with Anisomycin (Anis 0.5 µg/ml 15 min) or left untreated (NT). Cells were fixed and stained using the indicated Abs. The nuclei were detected using DAPI and slides were visualized using a spinning disc confocal microscope (Zeiss, ×100 magnification).

Figure 21:
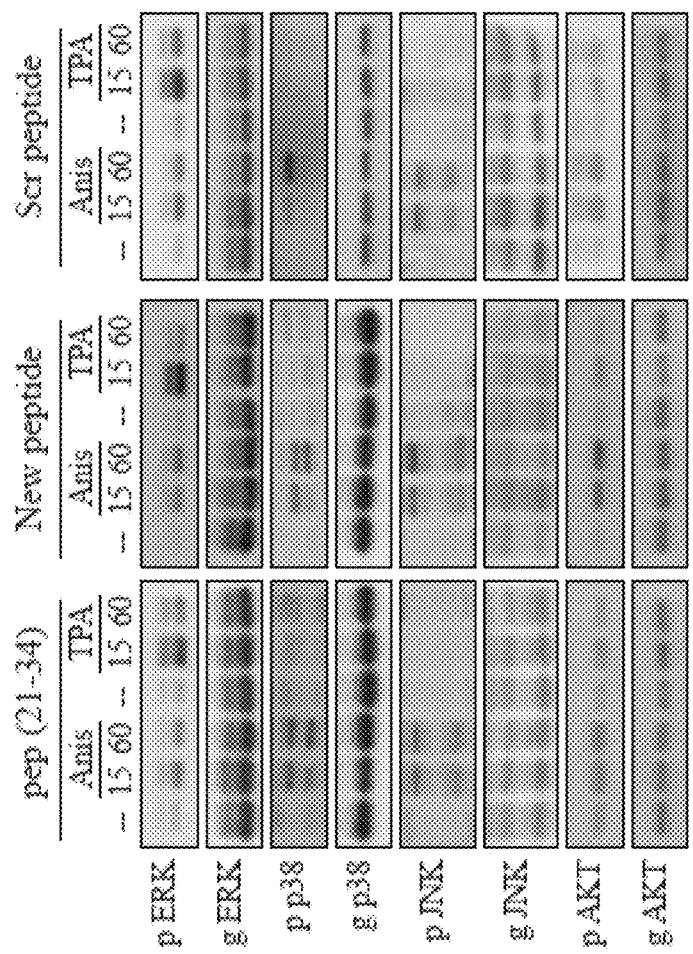

FIG. 21 illustrates that myristoylated peptides did not affect the stimulation-dependent activation of MAPKs. HeLa cells were grown to 70% confluence, serum starved and pre-incubated with either new peptide (NP), peptide or scrambled peptide and then either stimulated with Anisomycin (Anis 0.5 µg/ml), TPA (250 nM) or left untreated (NT). Cell extracts were produced and subjected to Western blot analysis with the indicated Abs.

DESCRIPTION OF SPECIFIC EMBODIMENTS OF THE INVENTION

The present invention, in some embodiments thereof, relates to peptides that may be used to prevent nuclear translocation of proteins which naturally associate with Imp7 as a means for translocating into the nucleus. The peptides may be used for the treatment of inflammatory and immunity related diseases. Further, the peptides may be used to promote nuclear translocation of proteins and other compounds into the cell nucleus when attached thereto.

The principles and operation of the nuclear localization signal according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

JNK and p38 are members of the mitogen activated protein kinase (MAPK) family. In mammals, there are three JNK isoforms (JNK1-3) and four p38 ones (p38α-δ) that regulate a large number of cellular processes, including mainly stress responses.

The present inventors studied the stimulated nuclear translocation of JNK1/2 and p38α/β, and found that all four rapidly translocate to the nucleus upon stress and mitogenic stimulations. Experimental results obtained by the inventors suggest that each of JNK1/2 and p38α/β are released from their cytoplasmic anchors by an activation-independent mechanism. This allows binding of either active or inactive MAPKs to either Imp7 or Imp9, bound to Imp3. The Imp3/Imp7 or Imp3/Imp9 dimers then escort the attached MAPKs to the nuclear envelope, where Imp3 remains, while Imp7/9 further penetrate through the nuclear pore. It is likely that the MAPK/Imp complex is then dissociated by GTP-Ran, which frees the MAPKs in the nucleus.

The present inventors next undertook to identify the site in JNK and p38 that mediate the interaction with Imp7 and Imp9 and showed that the important sequence lies within residues 20-30 of p38α (FIGS. 14A-14C).

Whilst reducing the present invention to practice, the present inventors synthesized a 14 amino acid myristoylated peptide based on the sequence of residues 21-34 of p38α and showed that when it was applied to HeLa cells prior to stimulation, it prevented the nuclear translocation (FIG. 4A), and Imp7/9 interactions (FIG. 4B) of the MAPKs examined.

Since the peptides of the present invention are able to specifically inhibit the nuclear activities of JNK1/2 and P38 α/β without modulating their cytoplasmic activities, these peptides may be used to inhibit JNK1/2 and P38 α/β nuclear activities (e.g. apoptotic activity, inflammatory activities) without harming other JNK1/2 and P38 α/β-related cytoplasmic activities in the cells. Therefore, the peptides of this aspect of the present invention may serve as therapeutic agent for inflammatory and apoptosis related diseases without having the side-effects of other JNK1/2 and p38 α/β inhibitors.

Thus, according to one aspect of the present invention there is provided an isolated peptide comprising an amino acid sequence being at least 80% homologous to the sequence as set forth in SEQ ID NO: 1, the isolated peptide comprising a nuclear targeting activity, the peptide being no longer than 20 amino acids.

According to another embodiment, the peptide comprises an amino acid sequence being at least 80% homologous to the sequence as set forth in SEQ ID NO: 2, comprises a nuclear targeting activity, and is no longer than 20 amino acids.

According to another embodiment, the peptide comprises an amino acid sequence being at least 80% homologous to the sequence as set forth in SEQ ID NO: 3, comprises a nuclear targeting activity, and is no longer than 20 amino acids.

According to another embodiment, the peptide comprises an amino acid sequence being at least 80% homologous to the sequence as set forth in SEQ ID NO: 4, comprises a nuclear targeting activity, and is no longer than 20 amino acids.

According to another embodiment, the peptide comprises an amino acid sequence being at least 80% homologous to the sequence as set forth in SEQ ID NO: 5, comprises a nuclear targeting activity, and is no longer than 20 amino acids.

According to another embodiment, the peptide comprises an amino acid sequence being at least 80% homologous to the sequence as set forth in SEQ ID NO: 6, comprises a nuclear targeting activity, and is no longer than 20 amino acids.

According to another embodiment, the peptide comprises an amino acid sequence being at least 80% homologous to the sequence as set forth in SEQ ID NO: 7, comprises a nuclear targeting activity, and is no longer than 20 amino acids.

According to another embodiment, the peptide comprises an amino acid sequence being at least 80% homologous to the sequence as set forth in SEQ ID NO: 8, comprises a nuclear targeting activity, and is no longer than 20 amino acids.

Thus, according to one aspect of the present invention there is provided an isolated peptide comprising an amino acid sequence being at least 80% homologous to the sequence as set forth in SEQ ID NO: 1, the isolated peptide capable of preventing the isolated peptide being capable of preventing P38α nuclear translocation, the peptide being no longer than 20 amino acids.

According to another embodiment, the peptide comprises an amino acid sequence being at least 80% homologous to the sequence as set forth in SEQ ID NO: 2, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 3, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 4, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 5, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 6, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 7, is capable of preventing the isolated peptide being capable of preventing P38α nuclear translocation, and is no longer than 20 amino acids.

According to another embodiment, the peptide comprises an amino acid sequence being at least 80% homologous to the sequence as set forth in SEQ ID NO: 8, is capable of preventing the isolated peptide being capable of preventing P38α nuclear translocation, and is no longer than 20 amino acids.

As mentioned, the peptides according to this aspect of the present invention are preferably no longer than 20 amino acids.

According to a particular embodiment, the peptides are 19 amino acids long.

According to a particular embodiment, the peptides are 18 amino acids long.

According to a particular embodiment, the peptides are 17 amino acids long.

According to a particular embodiment, the peptides are 16 amino acids long.

According to a particular embodiment, the peptides are 15 amino acids long.

According to a particular embodiment, the peptides are 14 amino acids long.

According to a particular embodiment, the peptides are 13 amino acids long.

According to a particular embodiment, the peptides are 12 amino acids long.

According to a particular embodiment, the peptides are 11 amino acids long.

According to a particular embodiment, the peptides are 10 amino acids long.

More preferably the homology to SEQ ID NOs: 1, 2, 3, 4, 5, 6, 7 or 8 of the amino acid sequence of the peptide of the present invention is 81 percent, more preferably 82 percent, more preferably 83 percent, more preferably 84 percent, more preferably 85 percent, more preferably 86 percent, more preferably 87 percent, more preferably 88 percent, more preferably 89 percent, more preferably 90 percent, more preferably 91 percent, more preferably 92 percent, more preferably 93 percent, more preferably 94 percent, more preferably 95 percent, more preferably 96 percent, more preferably 97 percent, more preferably 98 percent, more preferably 99 percent, and most preferably 100 percent.

According to one embodiment, the peptide of the present invention has an amino acid sequence which is identical to SEQ ID NO: 1, 2, 3, 4, 5, 6, 7 or 8.

According to still another embodiment, the peptide of the present invention consists of the amino acid sequence as set forth in SEQ ID NO: 1, 2, 3, 4, 5, 6, 7 or 8.

A percent homology or identity of a sample polypeptide to a reference polypeptide, such as that of the nuclear targeting peptide of the present invention to a polypeptide having an amino acid sequence set forth by SEQ ID NO: 1, 2 3, 4, 5, 6, 7 or 8 may be determined in any of various ways. Preferably, the percent homology or identity between polypeptides is determined using the Standard protein-protein BLAST [blastp] software of the NCBI.

The present inventors contemplate that the amino acid sequence of the peptides disclosed herein can be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

As used herein, the phrase "nuclear targeting activity" refers to the ability of the peptide to increase its nuclear: cytoplamic location ratio, or an agent linked thereto, by at least 10%, more preferably by at least 20% and even more preferably by at least 30%, 50%, 80% or more.

Nuclear targeting activity can be detected by either direct or indirect means: Direct observation by fluorescence or confocal laser scanning microscopy is possible when the nuclear targeting peptide is labeled with a fluorescent dye (labeling kits are commercially available, e.g. from Pierce or Molecular Probes). Nuclear targeting activity can also be assessed by electron microscopy if the nuclear targeting peptide is labeled with an electron-dense material such as colloidal gold (Oliver, Methods Mol. Biol. 115 (1999), 341-345).

It will be appreciated that if the nuclear targeting peptide is linked to a heterologous agent (e.g. a polynucleotide), then the activity may be detected by observing the location of the heterologous agent.

Nuclear targeting activity can be assessed in indirect ways if the linked molecule (e.g. nucleic acid) exerts a function in the nucleus. This function can be, for example, the expression of a gene encoded by the linked nucleic acid including the consequences of such gene expression that may be exerted on other cellular molecules or processes.

The term "peptide" or "polypeptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells. Thus, for example the present invention contemplates myristoylation of the peptide. Preferably the myristoylation occurs at the N terminal residue. Myristoylation is an irreversible, protein lipidation modification where a myristoyl group, derived from myristic acid, is covalently attached by an amide bond to the alpha-amino group of an N-terminal residue. Examples of myristoylated peptides contemplated by the present invention include SEQ ID NOs: 9-16.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2-NH—), hydroxyethylene bonds (—CH(OH)—CH2—), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| One-letter Symbol | Three-Letter Abbreviation | Amino Acid |
|---|---|---|
| A | Ala | Alanine |
| R | Arg | Arginine |
| N | Asn | Asparagine |
| D | Asp | Aspartic acid |
| C | Cys | Cysteine |
| Q | Gln | Glutamine |
| E | Glu | Glutamic Acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |
| X | Xaa | Any amino acid as above |

TABLE 2

| Code | Non-conventional amino acid | Code | Non-conventional amino acid |
|---|---|---|---|
| Hyp | Hydroxyproline | Orn | ornithine |
| Norb | aminonorbornyl-carboxylate | Abu | α-aminobutyric acid |
| Cpro | aminocyclopropane-carboxylate | Dala | D-alanine |
| Narg | N-(3-guanidinopropyl)glycine | Darg | D-arginine |
| Nasn | N-(carbamylmethyl)glycine | Dasn | D-asparagine |
| Nasp | N-(carboxymethyl)glycine | Dasp | D-aspartic acid |
| Ncys | N-(thiomethyl)glycine | Dcys | D-cysteine |
| Ngln | N-(2-carbamylethyl)glycine | Dgln | D-glutamine |
| Nglu | N-(2-carboxyethyl)glycine | Dglu | D-glutamic acid |
| Nhis | N-(imidazolylethyl)glycine | Dhis | D-histidine |
| Nile | N-(1-methylpropyl)glycine | Dile | D-isoleucine |
| Nleu | N-(2-methylpropyl)glycine | Dleu | D-leucine |
| Nlys | N-(4-aminobutyl)glycine | Dlys | D-lysine |
| Nmet | N-(2-methylthioethyl)glycine | Dmet | D-methionine |
| Norn | N-(3-aminopropyl)glycine | Dorn | D-ornithine |
| Nphe | N-benzylglycine | Dphe | D-phenylalanine |
| Nser | N-(hydroxymethyl)glycine | Dpro | D-proline |
| Nthr | N-(1-hydroxyethyl)glycine | Dser | D-serine |
| Nhtrp | N-(3-indolylethyl)glycine | Dthr | D-threonine |
| Ntyr | N-(p-hydroxyphenyl)glycine | Dtrp | D-tryptophan |
| Nval | N-(1-methylethyl)glycine | Dtyr | D-tyrosine |
| Nmgly | N-methylglycine | Dval | D-valine |
| Nmala | L-N-methylalanine | Dnmala | D-N-methylalanine |
| Nmarg | L-N-methylarginine | Dnmarg | D-N-methylarginine |
| Nmasn | L-N-methylasparagine | Dnmasn | D-N-methylasparagine |
| Nmasp | L-N-methylaspartic acid | Dnmasp | D-N-methylasparatate |
| Nmcys | L-N-methylcysteine | Dnmcys | D-N-methylcysteine |
| Nmgln | L-N-methylglutamine | Dnmgln | D-N-methylglutamine |
| Nmglu | L-N-methylglutamic acid | Dnmglu | D-N-methylglutamate |
| Nmhis | L-N-methylhistidine | Dnmhis | D-N-methylhistidine |
| Nmile | L-N-methylisolleucine | Dnmile | D-N-methylisoleucine |
| Nmleu | L-N-methylleucine | Dnmleu | D-N-methylleucine |
| Nmlys | L-N-methyllysine | Dnmlys | D-N-methyllysine |
| Nmmet | L-N-methylmethionine | Dnmmet | D-N-methylmethionine |
| Nmorn | L-N-methylornithine | Dnmorn | D-N-methylornithine |
| Nmphe | L-N-methylphenylalanine | Dnmphe | D-N-methylphenylalanine |
| Nmpro | L-N-methylproline | Dnmpro | D-N-methylproline |
| Nmser | L-N-methylserine | Dnmser | D-N-methylserine |
| Nmthr | L-N-methylthreonine | Dnmthr | D-N-methylthreonine |
| Nmtrp | L-N-methyltryptophan | Dnmtrp | D-N-methyltryptophan |
| Nmtyr | L-N-methyltyrosine | Dnmtyr | D-N-methyltyrosine |
| Nmval | L-N-methylvaline | Dnmval | D-N-methylvaline |
| Nmnle | L-N-methylnorleucine | Nle | L-norleucine |
| Nmnva | L-N-methylnorvaline | Nva | L-norvaline |
| Nmetg | L-N-methyl-ethylglycine | Etg | L-ethylglycine |
| Nmtbug | L-N-methyl-t-butylglycine | Tbug | L-t-butylglycine |
| Nmhphe | L-N-methyl-homophenylalanine | Hphe | L-homophenylalanine |
| Nmanap | αN-methyl-α-naphthylalanine | Anap | α-naphthylalanine |
| Nmpen | N-methylpenicillamine | Pen | penicillamine |
| Nmgabu | γN-methyl-γ-aminobutyrate | Gabu | γ-aminobutyric acid |

TABLE 2-continued

| Code | Non-conventional amino acid | Code | Non-conventional amino acid |
|---|---|---|---|
| Nmchexa | N-methyl-cyclohexylalanine | Chexa | cyclohexylalanine |
| Nmcpen | N-methyl-cyclopentylalanine | Cpen | cyclopentylalanine |
| Nmaabu | -α-amino-αN-methyl-methylbutyrate | Aabu | -methylbutyrateα-amino-α |
| Nmaib | -aminoisobutyrateαN-methyl- | Aib | -aminoisobutyric acidα |
| Marg | -methylarginineαL- | Dmarg | -methylarginineαD- |
| Masn | -methylasparagineαL- | Dmasn | -methylasparagineαD- |
| Masp | -methylaspartateαL- | Dmasp | -methylaspartateαD- |
| Mcys | -methylcysteineαL- | Dmcys | -methylcysteineαD- |
| Mgln | -methylglutamineαL- | Dmgln | -methylglutamineαD- |
| Mglu | -methylglutamateαL- | Dmglu | -methyl glutamic acidαD- |
| Mhis | -methylhistidineαL- | Dmhis | -methylhistidineαD- |
| Mile | -methylisoleucineαL- | Dmile | -methylisoleucineαD- |
| Mleu | -methylleucineαL- | Dmleu | -methylleucineαD- |
| Mlys | -methyllysineαL- | Dmlys | -methyllysineαD- |
| Mmet | -methylmethionineαL- | Dmmet | -methylmethionineαD- |
| Morn | -methylornithineαL- | Dmorn | -methylornithineαD- |
| Mphe | -methylphenylalanineαL- | Dmphe | -methylphenylalanineαD- |
| Mpro | -methylprolineαL- | Dmpro | -methylprolineαD- |
| Mser | -methylserineαL- | Dmser | -methylserineαD- |
| Mthr | -methylthreonineαL- | Dmthr | -methylthreonineαD- |
| Mtrp | -methyltryptophanαL- | Dmtrp | -methyltryptophanαD- |
| Mtyr | -methyltyrosineαL- | Dmtyr | -methyltyrosineαD- |
| Mval | -methylvalineαL- | Dmval | -methylvalineαD- |
| Mnva | -methylnorvalineαL- | Ncbut | N-cyclobutylglycine |
| Metg | -methylethylglycineαL- | Nchep | N-cycloheptylglycine |
| Mtbug | -methyl-t-butylglycineαL- | Nchex | N-cyclohexylglycine |
| Mhphe | -methyl-homophenylalanineαL- | Ncdec | N-cyclodecylglycine |
| Manap | -naphthylalanineα-methyl-α | Ncdod | N-cyclododecylglycine |
| Mpen | -methylpenicillamineα | Ncoct | N-cyclooctylglycine |
| Mgabu | -aminobutyrateγ-methyl-α | Ncpro | N-cyclopropylglycine |
| Mchexa | -methyl-cyclohexylalanineα | Ncund | N-cycloundecylglycine |
| Mcpen | -methyl-cyclopentylalanineα | Naeg | N-(2-aminoethyl)glycine |
| Nnbhm | N-(N-(2,2-diphenylethyl) carbamylmethyl-glycine | Nbhm | N-(2,2-diphenylethyl)glycine |
| Nnbhe | N-(N-(3,3-diphenylpropyl) carbamylmethyl-glycine | Nbhe | N-(3,3-diphenylpropyl)glycine |
| Tic | 1,2,3,4-tetrahydroisoquinoline-3-carboxylic acid | Nmbc | 1-carboxy-1-(2,2-diphenyl ethylamino)cyclopropane |
| pThr | Phosphothreonine | pSer | phosphoserine |
|  | O-methyl-tyrosine | pTyr | phosphotyrosine |
|  | Hydroxylysine |  | 2-aminoadipic acid |

The peptides of the present invention may comprise leader sequences to modulate secretion thereof in the cell. An exemplary leader sequence may comprise the TAT-leader sequence.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO-R1) and alkoxy carbonyl or aryloxy carbonyl groups (—CO—O-R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbornane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various bathers, through the gut, etc.); increased specificity, increased affinity, decreased toxicity and the like.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The compounds of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides and/or polypeptides of the present invention. These techniques may be preferred when the peptide is linked to a heterologous protein (i.e. a fusion protein) since recombinant techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Examples of heterologous proteins are provided hereinbelow.

To produce a peptide and/or polypeptide of the present invention using recombinant technology, a polynucleotide encoding the nuclear targeting peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention are inserted into expression vectors (i.e., a nucleic acid construct) to enable expression of the recombinant peptide. The expression vector of the present invention may include additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals). It will be appreciated that the expression vector may also comprise polynucleotide sequences encoding other polypeptides that are transcriptionally linked to the nuclear targeting peptides of the present invention. Such polypeptides are further described herein below.

A variety of prokaryotic or eukaryotic cells can be used as host-expression systems to express the peptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

It will be appreciated that the polynucleotides of the present invention may also be expressed directly in the subject (i.e. in vivo gene therapy) or may be expressed ex vivo in a cell system (autologous or non-autologous) and then administered to the subject. Gene therapy techniques are further described here in below.

Other than containing the necessary elements for the transcription and translation of the inserted coding sequence (encoding the polypeptide), the expression construct of the present invention can also include sequences engineered to optimize stability, production, purification, yield or activity of the expressed peptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston, Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant peptides and/or polypeptides of the present invention may either remain within the recombinant cell, secreted into the fermentation medium, secreted into a space between two cellular membranes, such as the periplasmic space in E. coli; or retained on the outer surface of a cell or viral membrane.

Following a predetermined time in culture, recovery of the recombinant peptide and/or polypeptide is effected.

The phrase "recovering the recombinant polypeptide" used herein refers to collecting the whole fermentation medium containing the polypeptide and need not imply additional steps of separation or purification.

Thus, peptides and/or polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The peptides and/or polypeptides of the present invention are preferably retrieved in "substantially pure" form.

As used herein, the phrase "substantially pure" refers to a purity that allows for the effective use of the protein in the applications described herein.

In addition to being synthesizable in host cells, the peptide and/or polypeptide of the present invention can also be synthesized using in vitro expression systems. These methods are well known in the art and the components of the system are commercially available.

As mentioned hereinabove, the polynucleotides of the present invention may also be administered directly into a subject where it is translated in the target cells i.e. gene therapy.

Gene therapy as used herein refers to the transfer of genetic material (e.g. DNA or RNA) of interest into a host to treat or prevent a genetic or acquired disease or condition or phenotype. The genetic material of interest encodes a product (e.g. a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ. The cells may be autologous or non-autologous to the subject. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

In in vivo gene therapy, target cells are not removed from the subject, rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

To confer specificity, preferably the nucleic acid constructs used to express the peptides and/or polypeptides of the present invention comprise cell-specific promoter sequence elements, such as cancer specific promoters (e.g. survivin promoter—Chen et al, Cancer Gene Therapy, 2004, Volume 11, Number 11, Pages 740-747).

For gene therapy, nucleic acids are typically introduced into cells by infection with viral agents. This is because higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

The nuclear targeting peptides of the present invention may be used to modulate nuclear translocation of both endogenous and exogenous polypeptides in host cells, including dividing (e.g. cell lines) and non-dividing cells (e.g. primary cells) and eukaryotic cells such as mammalian cells and yeast cells.

For example, the present inventors have shown that the nuclear targeting peptides of the present invention behave autonomously and compete with endogenous signals, such as those comprised in c-Jun N-terminal kinases 1/2 (JNK1/2) and p38 mitogen-activated protein kinase $\alpha/\beta$ (P38 $\alpha/\beta$). This results in down-regulation of the nuclear translocation of such endogenous signals.

Since the peptides of the present invention are able to specifically inhibit the nuclear activities of JNK1/2 and P38 $\alpha/\beta$ without modulating their cytoplasmic activities, these peptides may be used to inhibit JNK1/2 and P38 $\alpha/\beta$ nuclear activities (e.g. apoptotic activity, inflammatory activities) without harming other JNK1/2 and P38 $\alpha/\beta$-related cytoplasmic activities in the cells. Therefore, the peptides of this aspect of the present invention may serve as therapeutic agent for inflammatory and apoptosis related diseases without having the side-effects of other JNK1/2 and P38 $\alpha/\beta$ inhibitors.

Thus, according to another aspect of the present invention there is provided a method of treating an inflammatory or immune disorder in a subject, the method comprising administering to the subject a therapeutically effective amount of the isolated peptide described herein into the subject, thereby treating the inflammatory or immune disease.

As used herein, the term "subject" refers to a mammalian subject, preferably a human.

A number of diseases and conditions, which involve an inflammatory response can be treated using the methodology described hereinabove. Examples of such diseases and conditions are summarized infra.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost.2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

According to a particular embodiment of the present invention the disease is colitis.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

The present invention also anticipates preventing nuclear translocation of polypeptides that endogenously comprise the presently identified signal peptides by mutation of the identified sequences of the present invention by using knock-in strategies and the like.

Another means of modulating the nuclear translocation of endogenous polypeptides is by protein/protein interaction. Thus, for example, a nuclear targeting peptide linked to an antibody, may be introduced into a cell. The antibody recognizes and binds to its target polypeptide such that the target polypeptide becomes indirectly attached to the nuclear targeting peptide.

It will be appreciated that as well as functioning to modulate translocation of endogenous polypeptides, the peptides of the present invention may be linked to a heterologous substance via a linker, thereby acting as carriers, transporting the heterologous substance into the nucleus of a cell. It will be appreciated that the nuclear targeting peptide of the present invention may also attach to a heterologous substance in the cell and not in vitro. Thus the heterologous substance may be administered to the cell either prior to, concomitant with or following administration of the nuclear targeting peptide.

The heterologous substance may be any material which targeting thereof to the nucleus may be desired e.g. a pharmaceutical agent such as a therapeutic agent, a diagnostic agent or a cosmetic agent. Thus, according to this aspect of the present invention, the heterologous substance may be a polypeptide, a polynucleotide, a lipid, a carbohydrate, a hormone, a steroid, a small chemical, a virus and any combination thereof and the like.

According to an embodiment of this aspect of the present invention, the heterologous substance is a polypeptide. The polypeptide can be, for example, an immortalization protein (e.g., SV40 large T antigen and telomerase), an anti-apoptotic protein (e.g., mutant p53 and Bcl.sub.xL), an antibody, an oncogene (e.g., ras, myc, HPV E6/E7, and Adenovirus E1a), a cell cycle regulatory protein (e.g., cyclin and cyclin-dependent kinase), or an enzyme (e.g., green fluorescent protein, beta.-galactosidase, and chloramphenicol acetyl transferase).

According to another embodiment of this aspect of the present invention, the heterologous substance is a nucleic acid. The nucleic acid can be, e.g., RNA, DNA, or cDNA. The sequence of the nucleic acid can be a coding or a non-coding sequence (e.g., an antisense oligonucleotide).

The ability to safely and efficiently transfer nucleic acids into cells is a fundamental goal in biotechnology. Current synthetic delivery systems, although safe, are relatively inefficient. One of the major obstacles to efficient gene-delivery is targeting the genetic material into the nucleus. In current gene delivery methods, movement of DNA through the cytosol toward the nucleus occurs via diffusion, a relatively slow process during which the genetic material is exposed to a degrading cytoplasmic environment. Upregulating the efficiency of nuclear translocation of nucleic acids by incorporation of nuclear targeting peptides has already been accomplished—see for example Zanta et al., PNAS, Vol. 96, Issue 1, 91-96, Jan. 5, 1999; Subramanian, A. et al., (1999) Nat. Biotechnol. 17:873-877.

Thus the present inventors envision that the nuclear targeting peptides of the present invention will increase efficiency of various transfection protocols, including but not limited microinjection, electroporation, calcium phosphate coprecipitation, DEAE dextran introduction, liposome mediated introduction, viral mediated introduction, naked DNA injection, and biolistic bombardment.

According to yet another embodiment of this aspect of the present invention, the heterologous substance is a virus. The virus can be a whole virus or a virus core containing viral nucleic acid (i.e., packaged viral nucleic acid in the absence of a viral envelope). Examples of viruses and virus cores that can be transported include, but are not limited to, papilloma virus, adenovirus, baculovirus, retrovirus core, and Semliki virus core.

According to still another embodiment of this aspect of the present invention, the heterologous substance is a small molecule. The small molecule may be, for example a radionuclide, a fluorescent marker, or a dye.

According to an additional embodiment of this aspect of the present invention, the heterologous substance is a drug delivery system such as, e.g. magnetic particles, silica beads, PLGA, nano- or microspheres, chitosan etc.

According to yet another embodiment of this aspect of the present invention, the heterologous substance is an affinity moiety, such as an antibody, a receptor ligand or a carbohydrate. Linking of affinity moieties to the nuclear targeting peptides of the present invention is particularly beneficial when it is desirable to target a particular cell type with the nuclear targeting peptide. Examples of antibodies which may be used according to this aspect of the present invention include but are not limited to tumor antibodies, anti CD20 antibodies and anti-IL 2R alpha antibodies. Exemplary receptors include, but are not limited to folate receptors and EGF receptors. An exemplary carbohydrate which may be used according to this aspect of the present invention is lectin.

According to yet another embodiment of this aspect of the present invention, the heterologous substance is a detectable moiety.

The detectable moiety may be directly detectable typically by virtue of its emission of radiation of a particular wavelength (e.g. a fluorescent agent, phosphorescent agent or a chemiluminescent agent). Alternatively, the detectable moiety may be non-directly detectable. For example, the detectable agent moiety be a substrate for an enzymatic reaction which is capable of generating a detectable product.

It will be appreciated that the nuclear targeting peptides of the present invention may be linked to more than one heterologous substance either directly and/or indirectly.

The heterologous substance may be linked to the nuclear targeting peptide of the present invention by any method known in the art and which is appropriate for that particular heterologous substance. Thus for example, if the heterologous substance is a polypeptide, the linker may comprise a peptide bond or a substituted peptide bond, as described hereinabove. If the heterologous substance is a small molecule, the linker may comprise a non-peptide bond.

Examples of linking methods include, but are not limited to, chemical cross-linking, genetic fusion, and bridging.

Chemical Cross-Linking: Either a homobifunctional cross-linker or a heterobifunctional cross-linker can be used to cross-link a nuclear targeting peptide of the present invention with a heterologous substance. The homobifunctional or heterobifunctional cross-linker can be cleavable to facilitate separation of the nuclear targeting peptide from the heterologous substance after the nuclear targeting peptide transports the heterologous substance across a cell membrane. Homobifunctional cross-linkers have at least two identical reactive groups. Use of homobifunctional cross-linking agents may result in self-conjugation, intramolecular cross-linking and/or polymerization. Homobifunctional cross-linkers primarily are primary amine-reactive (e.g., imidoesters, N-succinimidyl esters, isothiocynates, carboxylic acids, and sulfonyl chlorides) or sulfhydryl reactive (e.g., 2-pyridyldithio, 3-nitro-2-pyridyldithio, maleimide, vinyl sulfone, aryl halide, dinitrofluorobenzene, organomercurial, p-chloromercuribenzoate, bismaleimidohexane, 1,5-difluoro-2,4-dinitrobenzene, and 1,4-di-(3'-(2'-pyrioyldithio)-propionamido) butane). Examples of homobifunctional imidoesters include, but are not limited to dimethyladipimidate, dimethylsuberimidate, and dithiobispropionimidate. Examples of homobifunctional NHS esters include, but are not limited to, disuccinimidyl glutarate, disuccinimidyl suberate, bis(sulfosuccinimidyl) suberate, dithiobis(succinimidyl propionate), and disuccinimidyl tartarate.

Heterobifunctional cross-linkers possess two or more different reactive groups that allow for sequential conjugation with specific groups, thus minimizing undesirable polymerization or self conjugation. Some heterobifunctional cross-linkers are amine reactive at one end and sulfhydryl reactive at the other end. Examples of such cross-linking agents include, but are not limited to, succinimidyl 4-(N-maleimidomethyl) cyclohexane-1-carboxylate, m-maleimidobenzyl-N-hydroxysuccinimide ester, succinimidyl 4-(p-maleimidophenyl)-butyrate, bismaleimidohexane, and N-(g-maleimidobutyryloxy) succinimide ester.

The homobifunctional or heterobifunctional cross-linking reactions can be stopped after adding linking the homobifunctional or heterobifunctional cross linker to the nuclear targeting peptide. The nuclear targeting peptide with a homobifunctional or heterobifunctional cross-linking agent can be purified by methods well known in the art and used as a stock for adding heterologous substances. Such purified nuclear targeting peptides with the attached homobifunctional or heterobifunctional cross-linking reagent can be stored, for example at −20° C. in aliquots and subsequently thawed. Once thawed a heterologous substance can be added by completing the cross-linking reaction.

Genetic Fusion: Genetic fusions can be generated by linking a coding sequence for a nuclear targeting peptide in-frame with a coding sequence for a polypeptide heterologous substance. Many methods exist in the art for linking coding sequences together. Exemplary methods include, but are not limited to, polymerase chain reaction (PCR), stitch PCR, and restriction endonuclease digestion and ligation. Preferably the reading frames of the nuclear targeting peptide and the heterologous substance are in frame and transcriptionally fused.

A protease cleavage site can be included between the nuclear targeting peptide and the polypeptide heterologous substance. Examples of such protease cleavage sites include, but are not limited to Factor Xa and tobacco etch virus (TEV) protease.

Bridging Molecules: Nuclear targeting peptides and heterologous substances can be complexed using pairs of bridging molecules. Examples of such pairs include, but are not limited to, (a) streptavidin and biotin, (b) glutathione and glutathione-S-transferase, and (c) polyhistidine and an affinity chromatography reagent (e.g., tetradentate nitrilotriacetic acid (NTA) or iminodiacetic acid (IDA)), which interact through an ion such as $Ni^{+2}$. A nuclear targeting peptide can be linked to either member of the pair, and a heterologous is linked to the other bridging molecule. For example, if the nuclear targeting peptide is linked to glutathione-S-transferase then the cargo is linked to glutathione. Alternatively, the nuclear targeting peptide may be linked to streptavidin and the heterologous substance may be linked to biotin. The nuclear targeting peptide and the streptavidin can be linked by any method known in the art for linking a peptide and a bridging molecule. Examples of such methods include, but are not limited to, chemical cross-linking or genetic fusion. The heterologous substance is then linked to biotin by any method known in the art for biotinylating small molecules, proteins, or nucleic acids, such as chemical cross-linking. The nuclear targeting peptide/heterologous substance complex can be formed by contacting the nuclear targeting peptide-streptavidin with the biotinylated heterologous substance.

A nuclear targeting peptide and heterologous substance can be complexed chemically or using pairs of bridging molecules at any position on either the nuclear targeting peptide or the heterologous substance, providing that functionality of either the nuclear targeting peptide or heterologous substance is not destroyed. For example, a cross-linking agent will react with appropriate functional groups located at the amino-terminus or carboxy-terminus (for proteins), at the 5' end or 3' end (for nucleic acids), or throughout the molecule.

A skilled artisan will be able to determine if the respective parts of the nuclear targeting peptide/heterologous substance complex retains biological activity. The nuclear targeting peptide retains biological activity if it can translocate the linked heterologous substance into a cell nucleus. Transport activity can be ascertained, for example, by adding the nuclear targeting peptide/heterologous substance complex to cells and assaying the cells to determine if the heterologous substance was delivered across into the nucleus using methods known in the art such as immunohistochemical staining. The heterologous substance can be assayed for activity using a method acceptable for the type of heterologous substance (e.g., an enzyme assay for an enzyme, a transformation assay for an oncoprotein, an anti-apoptotic assay for an anti-apoptosis protein, and an immortalization assay for an immortalization protein). These assays are well known in the art and are described in Sambrook et al., 1989 and Ausubel et al., 1989.

If the nuclear targeting peptide and polypeptide heterologous substance are genetically linked, the polypeptide cargo moiety can be complexed to either the amino terminus of the nuclear targeting peptide or to the carboxy-terminus of the nuclear targeting peptide. Preferably, the polypeptide cargo moiety is complexed to the N terminus of the nuclear targeting peptide.

The nuclear targeting peptides of the present invention may be administered to the cells per se or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nuclear targeting peptides of the present invention either alone or linked to a heterologous agent, or polynucleotides encoding same, which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

A recombinant vector can be administered in several ways. If vectors are used which comprise cell specific promoters, for example, the procedure can take advantage of their target specificity and consequently, do not have to be administered locally at the diseased site.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p.1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the polypeptides and polynucleotides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

DNA Constructs and mutations: GFP-JNK1/2, p38α/β were cloned in pEGFP-C1 (Clontech, Mountain View, Calif.). JNK1/2 and p38α/β sequences were amplified from HeLa cells cDNA and flanked by EcoRI/BamHI for JNK2 and p38β, and with XhoI/BamHI for JNK1 and p38α. Point mutations of JNK1/2 and p38α/β were performed by site-directed mutagenesis. GST-JNK1/2, p38α/β were cloned in pGEX-2T vector (GE healthcare, Buckinghamshire, UK) and flanked by SpeI/NotI restriction sites. Deletion mutation of either N and C-terminal of GFP-p38α were performed using specific primers to construct Δ7/Δ20/Δ30 N-terminal deletion mutation or Δ40 C-terminal deletion mutation. Importin 3, 7 and 9 were cloned in pEGFP-C. Importin 7 and 9 were amplified from HeLa cells cDNA using specific primers flanked by BamHI/SalI for Importin 7 and XhoI/SalI for Importin 9, restriction sites. Importin 3 was acquired from Forchheimer repository plasmid collection, and amplified using specific primers flanked by XhoI/EcoRI restriction sites.

Cell Culture and transfection: HeLa and MCF7 cells were cultured in Dulbecco's modified Eagle's medium (DMEM) supplemented with 2 mM L-glutamine, 1% Pen/Strep and 10% fetal bovine serum (FBS). HB2 cells were cultured in the same medium with the addition of hydrocortisone (0.5 mg/ml), and insulin (10 µg/ml). MCF10A cells were cultured in DMEM/F-12 with 5% horse serum, EGF (200 ng/ml), hydrocortisone (0.5 mg/ml), cholera toxin (100 ng/ml), insulin (10 µg/ml), 2 mM L-glutamine, 1% pen/strep and 10% FBS. All cells were maintained at 37° C. in a humidified atmosphere of 95% air and 5% CO2. HeLa cells were transfected using polyethylenimine (Sigma). siRNAs were transfected using Dharmafect (Thermo Fisher Scientific, CO, USA).

Immunofluorescence microscopy: Cells were fixed in 3% paraformaldehyde in PBS (20 min, 23° C.), and incubated with 2% Albumin bovine serum (BSA) in PBS (15min, 23° C.), followed by permeabilization with Triton X-100 (0.1% in PBS, 5 min, 23° C.). The fixed cells were then incubated with the primary Abs (60 min, 23° C.), washed three times with PBS and incubated with rhodamine-conjugated secondary Ab (60 min, 23° C.), and DAPI. Slides were visualized by fluorescence microscope (Olympus BX51, ×40 magnification). Background correction, and contrast adjustment of raw data images were performed using Photoshop (Adobe, Calif., USA).

Co-Immunoprecipitation: HeLa cells were grown to sub-confluency, serum-starved (0.1% FBS for 16 h) and then stimulated or treated with other drugs. Cell extracts were produced as previously described and incubated for 2 hours (4° C., with rotation) with A/G-agarose beads (Santa Cruz Biotechnology) pre-linked with specific Abs (1 hrs, 23° C.). The bound A/G beads were washed three times with ice-cold washing buffer. The IPed beads were then resuspended with 1.5× sample buffer and boiled; the resolved proteins were analyzed by Western blotting with the indicated Abs.

Proximity ligation assay (PLA): Protein-protein interactions were detected with Duolink PLA Kit (Olink Bioscience), according to the manufacturer's protocol. Briefly, cells were grown, fixed and permeabilized as described. The samples were then incubated with primary Abs against two examined proteins (60 min, 23° C.), washed, (0.01 M Tris HCl pH 7.4, 0.15 M NaCl and 0.05% Tween 20), and then incubated with specific probes (60 min, 37° C.), following by DAPI staining to visualize nuclei and wash with Buffer B: 0.2 M Tris HCl pH 7.5, 0.1 M NaCl. The signal was visualized as distinct fluorescent spots by fluorescence microscope (Olympus BX51, ×40 magnification). Background correction, contrast adjustment of raw data images and the quantification of the fluorescence signal were performed using Photoshop (Adobe) and ImageJ.

In-vitro interaction: HeLa cells were grown to subconfluency, serum-starved (0.1% FBS for 16 h) and then treated with stimuli or other drugs. Cell extracts were produced as described and incubated for 2 hrs (4° C.) with A/G-agarose beads (Santa Cruz Biotechnology) pre-linked with specific Abs (1 hr, 23° C.). The bound A/G beads were sequentially washed once with RIPA buffer, then twice with 0.5M LiCl and twice with Buffer A. The bound A/G beads were then resuspended in Buffer A containing 0.01% BSA and aliquoted. GST tagged proteins were incubated with the beads 2 hrs (4° C.) then washed and resuspended in 1.5 × sample buffer and boiled.

Gel filtration: HeLa cells were serum starved (as above) and then were either stimulated with Anisomycin (Anis, 0.5 µg/ml, 15 min) and TPA (250 nM, 15 min), or left untreated (NT). Cell extracts (25 mg of each treatment) were loaded on a 16/60 superdex 200 sizing column (flow rate 1 ml/min), and 1 ml fractions were collected. The fractions were analyzed using Western blot with the appropriate Abs.

Statistical Analysis: Data are expressed as mean±S.E. Statistical evaluation was carried out using functional analysis and Student's t test (two-tailed) to test for differences between the control and experimental results. Values of $p<0.05$ were considered statistically significant.

Example 1

JNK and p38 Translocate into the Nucleus Using a NTS-Independent Mechanism

In the search for NLS-independent shuttling proteins, the present inventors have looked into the subcellular localization of JNK1/2 and p38α/β. Using immunostaining with specific antibodies (Abs) it was found that, similar to ERK1/2, JNK1/2 and p38α/β are localized mainly in the cytoplasm of resting cells (FIG. 7A and FIGS. 8A-8B). Treating the cells with either stress or mitogenic stimulants (Anisomycin and TPA, respectively), a rapid and robust nuclear translocation of all four MAPK isoforms was observed, with only minor differences in their kinetics of translocation. Interestingly, this translocation did not correlate with JNK1/2 and p38α/β activatory phosphorylation (FIG. 7B), indicating that the mechanism of translocation of these four MAPKs is different from that of ERK1/2. Moreover, none of the JNK or p38 proteins contained an NTS, and only two, JNK2 and p38β, contained a phosphorylatable sequence (T-P-S) in the same kinase region. However, the pronounced sequence and conformation similarities among JNK1/2 and p38α/β to ERK1/2, may suggest that the former still use a NTS-like sequence within their kinase insert domain for their translocation. To exclude this possibility, the present inventors mutated the phosphorylated NTS-aligned residues in JNK1 or p38α to either Ala or Glu residues in all four MAPKs. Unlike ERK1/2, overexpression of these mutants resulted in a similar distribution to that of WT proteins (FIG. 9), indicating that JNK1/2 and p38α/β differ from ERK1/2 not only in the release from anchoring protein, but also in their mechanism of translocation.

Example 2

JNK1/2 and p38α/β Interact with Imp3, 7 and 9 Upon Stimulation

The lack of ERK1/2-like NTS, as well as a canonical or any atypical NLSs, and the inability of JNK1/2 and p38α/β to interact with either Impα or Impβ either directly or indirectly, prompted the search for their actual mechanism of translocation. Since β-like Imps (Table 3 herein below) have been implicated in the stimulated translocation of signaling proteins, it was hypothesized that one or more of these Imps are involved in the process. To examine this, a co-immunoprecipitation (CoIP) screen was used to detect whether any of them could interact with JNK1/2 and p38α/β. Despite the expression of these Imps in the examined cells, no significant Imp/MAPK interactions were detected in resting HeLa cells (FIG. 1A). However, IP of JNK1/2 and p38α/β, in extracts of stimulated HeLa cells, revealed a varying degree of interaction of all four MAPKs with Imps 3, 7 and 9. Importantly, the screen, and other IP experiments demonstrated only small differences in association or timing of interactions between the components, suggesting a similar mode of regulation among them.

TABLE 3

List of Impβ-like proteins

| Examples of signaling proteins as "cargos" | Acronyms | Importin |
|---|---|---|
| Acting with or without Importin-α to induce translocation of several signaling proteins[1] | Kapβ1, IMB1, IPOB, KPNB1 | Importin-β |
| c-Jun[2], NPM-ALK[3], YBP1[3], EWS[4] | TNPO1, IMB2, MIP1, Kapβ2 | Importin2 |
| No known signaling molecules | TNPO2, KPNB2B, Trn-SR | Importin3 |
| VitD Rec.[5], HIF1-α[6] | IMB4, RanBP4 | Importin4 |
| c-Jun[2], p60TRP[7] | IMB3, RANBP5, Kapβ3, KPNB3 | Importin5 |
| ERK1/2[8, 9], MEK1[8], SMAD3/4[8, 10] Egr1[11], HIF1α[6], c-Jun[2], Glucocorticoid Rec.[12] | RANBP7 | Importin7 |
| SMAD1/3/4[10], NPM-ALK[3] | RANBP8 | Importin8 |
| PR65 of PP2A[13], c-Jun[2] | IMB5 | Importin9 |

TABLE 3-continued

List of Impβ-like proteins

| Examples of signaling proteins as "cargos" | Acronyms | Importin |
|---|---|---|
| No known signaling molecules MLF2[14], RBM4[14] | RanBP11, KA120 TNPO3, TRN-SR(1-3), MTR10A | Importin11 Importin12 |
| Glucocorticoid Rec.[15], c-Jun[2] | KAP13, RANBP13, LGL2 | Importin13 |

References for Table 3.
[1]Chook, Y. M. & Suel, K. E. Nuclear import by karyopherin-betas: recognition and inhibition. Biochim Biophys Acta 1813, 1593-1606 (2011).
[2]Waldmann, I., Walde, S. & Kehlenbach, R. H. Nuclear import of c-Jun is mediated by multiple transport receptors. J Biol Chem 282, 27685-27692 (2007).
[3]Wu, F., Wang, P., Young, L. C., Lai, R. & Li, L. Proteome-wide identification of novel binding partners to the oncogenic fusion gene protein, NPM-ALK, using tandem affinity purification and mass spectrometry. Am J Pathol 174, 361-370 (2009).
[4]Zakaryan, R. P. & Gehring, H. Identification and characterization of the nuclear localization/retention signal in the EWS proto-oncoprotein. J Mol Biol 363, 27-38 (2006).
[5] Miyauchi, Y. et al. Importin 4 is responsible for ligand-independent nuclear translocation of vitamin D receptor. J Biol Chem 280, 40901-40908 (2005).
[6]Chachami, G., Paraskeva, E., Georgatsou, E., Bonanou, S. & Simos, G. Bacterially produced human HIF-1 alpha is competent for heterodimerization and specific DNA-binding. Biochem Biophys Res Commun 331, 464-470 (2005).
[7]Heese, K. et al. Characterizing the new transcription regulator protein p60TRP. J Cell Biochem 91, 1030-1042 (2004).
[8]Chuderland, D., Konson, A. & Seger, R. Identification and characterization of a general nuclear translocation signal in signaling proteins. Mol Cell 31, 850-861 (2008).
[9] Lorenzen, J. A. et al. Nuclear import of activated D-ERK by DIM-7, an importin family member encoded by the gene moleskin. Development 128, 1403-1414 (2001).
[10] Yao, X., Chen, X., Cottonham, C. & Xu, L. Preferential utilization of Imp7/8 in nuclear import of Smads. J Biol Chem 283, 22867-22874 (2008).
[11]Chen, J., Liu, M. Y., Parish, C. R., Chong, B. H. & Khachigian, L. Nuclear import of early growth response-1 involves importin-7 and the novel nuclear localization signal serine-proline-serine. Int J Biochem Cell Biol 43, 905-912 (2011).
[12] Freedman, N. D. & Yamamoto, K. R. Importin 7 and importin alpha/importin beta are nuclear import receptors for the glucocorticoid receptor. Mol Biol Cell 15, 2276-2286 (2004).
[13]Lubert, E. J. & Sarge, K. D. Interaction between protein phosphatase 2A and members of the importin beta superfamily. Biochem Biophys Res Commun 303, 908-913 (2003).
[14]Lai, M. C., Kuo, H. W., Chang, W. C. & Tarn, W. Y. A novel splicing regulator shares a nuclear import pathway with SR proteins. Embo J 22, 1359-1369 (2003).
[15] Tao, T., Lan, J., Lukacs, G. L., Hache, R. J. & Kaplan, F. Importin 13 regulates nuclear import of the glucocorticoid receptor in airway epithelial cells. American journal of respiratory cell and molecular biology 35, 668-680 (2006).

To verify these interactions, the CoIP experiments were repeated in MCF7 cells, and the interactions of overexpressed MAPKs with the Imps were examined in HeLa cells. Both experiments confirmed that the IP of Imp3/7/9 are not specific to endogenous HeLa proteins only (FIGS. 10A-10B). In addition, a proximity ligation assay (PLA) was performed, which is a CoIP-independent tool for protein-protein interaction studies. Similar to the CoIP results, no significant basal interactions between the examined Imps and MAPKs were detected (FIG. 1B). However, Anisomycin or TPA stimulation resulted in a marked increase in the interaction of either JNK1/2 or p38α/β with Imps 3/7/9. As would be expected from the shuttling role of the Imps, the interactions were found mostly in the cytoplasm and peri-nuclear regions. These results indicate that the stimulated interaction of Imps 3/7/9 with the MAPKs first occurs in the cytoplasm and the importins are detached from the MAPKs either during the shuttling, or immediately after translocation.

Example 3

Imp3, 7 and 9 are Required for JNK1/2 or p38α/β Translocation into the Nucleus

To further substantiate the role of Imp3/7/9 in the nuclear translocation of JNK1/2 or p38α/β, knockdown experiments were performed using their Si-RNA. A knockdown of Imp5, and a non-relevant Si-RNA served as controls. The Si-RNAs of the four Imps examined reduced the amount of the relevant Imps by more than 85% within 48 hr (FIGS. 2A-2C). These knockdowns did not affect the cytoplasmic localization of endogenous JNK1/2 or p38α/β in resting cells. However, the knockdown of Imp3/7/9, but not Imp5 or Si-control, strongly modulated the stimulated nuclear shuttling of the examined MAPKs. The knockdown of Imp3 inhibited the translocation in ~80% of the cells, whereas the Si-RNA of Imp7 and Imp9 prevented the translocation only in ~60%. To further study the effect of Imp3/7/9 knockdown on the translocation of JNK1/2 or p38α/β, the present inventors examined the phosphorylation of the nuclear JNK/p38 substrates c-Jun, ATF-2 and MEF2A. Importantly, all three Si-RNAs significantly inhibited the stimuli-induced phosphorylation of these transcription factors, although the effect of the Si-RNA of Imp3 was somewhat higher than that of Imp7/9 (FIG. 2C). No effect on the ERK target C-Myc (FIG. 11) or other off-target effects of the Si-RNAs were detected in any other proteins examined. Thus, it appears that the three Imps are important for the translocation of both JNK1/2 and p38α/β, although the role of Imp3 might be more general.

In order to participate in the translocation process, it is possible that unlike Impα/β, Imps 3/7/9 change their localization upon stimulation. Indeed, it was found (FIGS. 12A-12B) that stimulation of both HeLa and HB2 cells cause a significant shift of Imp3/7/9 from the cytoplasm to either the perinuclear region (Imp3), or into the nucleus (Imp7/9). Impβ localization was not affected at all upon stimulation. The results suggest that all three Imps are important for the nuclear translocation of JNK1/2 or p38α/β, which may act either interchangably, or probably via formation of translocation complexes. Finally, as would be expected by the dependence of β-like Imps on Ran activity, using Si-RNA of Ran it was found that the translocation of JNK and p38 is indeed Ran-dependent (FIG. 13). These observations suggest a role for the β-like Imps in stress- and mitogenic-induced processes, implicating them in transcription regulation upon cellular stimulation.

Example 4

JNK1/2 and p38α/β Interact with Either Imp7 or Imp9, Via a Specific N-Terminal Sequence To obtain a better insight into the MAPKs-Imps interaction, the present inventors looked into the in vitro interaction of GST-p38α/β and GST-JNK1/2 with Imps from extracts of non-stimulated or stimulated HeLa cells. Although the MAPKs interacted with Imp7/9 from stimulated cells as expected, no in-vitro interaction was detected with Imp3 (FIG. 3A). Moreover, CoIP experiment revealed that Imp 3 is not required for the interaction of JNK and p38 with Imp7/9 (FIG. 3B vs FIG. 1A). These results show that JNK and p38 interact directly with Imp7 or Imp9 only, and do not require Imp3 for this interaction.

The present inventors next undertook to identify the site in JNK and p38 that mediate the interaction with Imp7 and Imp9. For this purpose, various regions in the C and N terminal regions adjacent to the kinase domain of p38α were deleted, and these deletions were examined as to their affect on subcellular localization and importin interaction of the kinase (FIGS. 14A-14C). Both deletion of the N and C terminal domain resulted in the cytosolic localization of p38α, however, only the N terminal deletion (AA 1-30) prevented the stimulated translocation and Imp7/9 interactions, pointing to the importance of this region for the translocation. In order to locate the exact sequence that is required for the translocation, the present inventors further subdivided the N-terminus, by deleting either the first 7 or 20 residues of the kinase. Importantly, these two additional mutations had no effect on the translocation or the binding to Imp7/9, strongly suggesting that the important sequence lies within residues 20-30 of p38α.

To further study the role of the identified region in the nuclear translocation of the MAPKs, the present inventors synthesized a 14 amino acid myristoylated peptide, based on the sequence of residues 21-34 of p38α (Peptide sequence: Myr-PERYQNLSPVGSGA—SEQ ID NO: 16). Since this region is similar in p38β as well as in JNK1 and JNK2, it was hypothesized that it should compete with the interaction of all four MAPKs with Imp7/9 and thereby affect their nuclear translocation. Indeed, when this peptide was applied to Hela cells prior to stimulation, it prevented the nuclear translocation (FIG. 4A), and Imp7/9 interactions (FIG. 4B) of the MAPKs examined. Thus, these results clearly verify the importance of the N-terminal residues in the JNK/p38 isoforms in regulating their nuclear translocation, and suggest that this peptide can be used to study the role of the translocation and its clinical involvement.

Example 5

Imp719-JNK/p38 Complex Interact with Phosphorylated Imp3

The interaction of the MAPKs with Imp3/7/9 in cells (FIGS. 1A-1B) raised the question as to what is the role of each of the Importins in the process of nuclear translocation. The fact that the SiRNA of Imp3 had a higher effect than that of Imp7/9 (FIGS. 2A-2C), that Imp3 did not directly interact with JNK1/2 or p38α/β in vitro (FIG. 3A), and that Imp3 is not required for the MAPKs interactions with Imp7/9 (FIG. 3B) led to the hypothesis that the MAPKs bind either to Imp7 or Imp9, and then Imp3 joins the dimers to allow their nuclear translocation.

In order to examine this hypothesis, and establish a complex formation between endogenous Imp3/7/9, the present inventors monitored these possible interactions by PLA. No interaction between any of the examined Importins was detected in resting HeLa cells (FIGS. 5A, 5B). However, this was dramatically changed upon stimulation, which induced interaction between Imp3 and either Imp7 or Imp9, but not between Imp7 and Imp9. These results were then confirmed by CoIP experiments of stimulated extracts from HeLa cells as well (FIG. 5C). Interestingly, in vitro interaction of recombinant Imp7 and Imp9 with Imp3 from non-stimulated or stimulated cells (FIG. 5D) demonstrated that Imp3 is modified upon stimulation to allow the interaction. Treatment of the cell extract with alkaline phosphatase (CIP) reduced the interaction, strongly indicating that the interaction with Imp7/9 requires the phosphorylation of Imp3.

Example 6

Gel Filtration Analysis of MAPKs-Imps Interactions

To further validate this mechanism, gel filtration was performed to separate unbound proteins from higher MW complexes. Indeed, Imp3/7/9 from resting cells appeared at their expected monomeric MW (~90 kDa for Imp3 and ~120 kDa for Imp7/9; FIG. 5A). Imp3 also appeared in a ~160 kDa peak, which may represent either a homo or hetero dimer/trimer of the protein. Interestingly, a small amount of all three non-stimulated Imps was detected in another, 220-400 kDa (designated as ~280 kDa) peak (FIG. 6A). This relatively wide ~280 peak may correspond to either a dimer of Imps, a heterotrimer containing a dimer of Imps with additional 30-80 kDa proteins (e.g. MAPKs), or a complex of the Imps with any high MW proteins (100-200 kDa). Importantly, the relative amount of the Imps in the various peaks was dramatically changed in extracts from stimulated cells. Thus, the amount of Imps3/7/9 in the lower MW peaks significantly decreased, while that of the higher ones correspondingly increased. In parallel, JNK, and p38 shifted from a sharp peak at ~40 kDa, to a very wide peak after stimulation (FIGS. 15A-15B).

In order to ascertain that the higher MW peaks of the Imps and MAPKs are formed, at least partially, by interaction between MAPKs and dimers of Imps, CoIP experiments were performed. As expected, no association between the components was detected in the ~120 kDa peaks (FIG. 6B); this was also true for the higher MW peak (~160 kDa) of Imp3. On the other hand, Imp3/7/9 CoIPed both JNK and p38 proteins from the stimulated, 280 kDa peak. In addition, the Imp3 CoIPed both Imp7 and Imp9, while no interaction between Imp7 and Imp9 was detected. The lack of interaction between Imp7 and Imp9 was observed in higher MW fractions as well, clearly indicating that no Imp3/7/9 trimers are formed after stimulation. No reproducible differences in MAPKs/Imps binding affinity was detected under the distinct stimulations, indicating redundant activities of the dimers with MAPKs. These results further support the present notion that upon stimulation, Imp3 interacts with dimers of either Imp7/MAPK or Imp9/MAPK, and the heterotrimers are required for the proper translocation to the nucleus.

Example 7

Use of the Myristoylated Peptides for the Treatment of Colitis

Materials and Methods

Cell Culture and transfection: HeLa cells were cultured in Dulbecco's modified Eagle's medium (DMEM) supplemented with 2 mM L-glutamine, 1% Pen/Strep and 10% fetal bovine serum (FBS).

Immunofluorescence microscopy: Cells were fixed in 3% paraformaldehyde in PBS (20 min, 23° C.), and incubated with 2% Albumin bovine serum (BSA) in PBS (15 min, 23° C.), followed by permeabilization with Triton X-100 (0.1% in PBS, 5 min, 23° C.). Cells were incubated with the primary Abs (60 min, 23° C.), washed three times with PBS and incubated with rhodamine-conjugated secondary Ab (60 min, 23° C.), and DAPI. Slides were visualized by either fluorescence microscope (Olympus BX51, ×40 magnification), or spinning disk confocal microscope (Zeiss, Cell observer SD, ×100 magnification). Background correction, and contrast adjustment of raw data were performed using Photoshop (Adobe, Calif., USA).

DNA Constructs and mutations: GFP-JNK1/2, p38α/β were cloned in pEGFP-C1 (Clontech, Mountain View, Calif.). JNK1/2 and p38α/β sequences were amplified from HeLa cells cDNA and flanked by EcoRI/BamHI for JNK2 and p38β, and with XhoI/BamHI for JNK1 and p38α. Point mutations of JNK1/2 and p38α/β were performed by site-directed mutagenesis. GST-JNK1/2, p38α/β were cloned in pGEX-2T vector (GE healthcare, Buckinghamshire, UK) and flanked by SpeI/NotI restriction sites. Deletion mutation of either N and C-terminal of GFP-p38α were performed using specific primers to construct 47/420/430 N-terminal deletion mutation or Δ40 C-terminal deletion mutation. Importin 3, 7 and 9 were cloned in pEGFP-C. Importin 7 and 9 were amplified from HeLa cells cDNA using specific primers flanked by BamHI/SalI for Importin 7 and XhoI/SalI for Importin 9, restriction sites. Importin 3 was acquired from Forchheimer repository plasmid collection, and amplified using specific primers flanked by XhoI/EcoRI restriction sites.

Myristoylated peptide: Myristoylated peptide was specifically designed (peptide2.0, VA, USA). Peptide sequences: KPERYQNLSPVGSGA—SEQ ID NO: 9 (residues 21-34 of p38α) and KPERYQNLSPVAAAA (SEQ ID NO: 10).

CoIP: Cell extracts were produced and incubated for 2 hr (4° C., with rotation) with A/G-agarose beads pre-linked with specific Abs (1 hr, 23° C.). The bound A/G beads were washed, resuspended (1.5× sample buffer), boiled and subjected to Western blotting.

Proximity ligation assay (PLA). Protein-protein interactions were detected with Duolink PLA Kit; Olink Bioscience), according to the manufacturer's protocol. Briefly, cells were grown, fixed and permeabilized as described. The samples were then incubated with primary Abs against two examined proteins (60 min, 23° C.), washed (0.01 M Tris HCl pH 7.4, 0.15 M NaCl and 0.05% Tween 20), and then incubated with specific probes (60 min, 37° C.), following by DAPI staining to visualize nuclei and washed (0.2 M Tris HCl pH 7.5, 0.15 M NaCl). The signal was visualized as distinct fluorescent spots by a fluorescence microscope (Olympus BX51, ×40 magnification). Background correction, contrast adjustment and the quantification of the fluorescence signal were performed using Photoshop and ImageJ.

In vitro interaction assay: Cell extracts were produced as described and incubated for 2 hr (4° C.) with A/G-agarose beads pre-linked with specific Abs (1 hr, 23° C.). The bound A/G beads were sequentially washed with RIPA buffer, twice with 0.5M LiCl and twice with Buffer A. The bound A/G beads were then resuspended in Buffer A containing 0.01% BSA and aliquoted. GST tagged proteins were incubated with the beads 2 hr (4° C., with rotation) then washed and resuspended in 1.5 × sample buffer and boiled.

In vitro phosphatase assay: HeLa cells were grown to subconfluency, serum-starved (0.1% FBS for 16 hr) and then treated with stimuli or other drugs. Cell extracts were produced as described and incubated for 2 hr (4° C., with rotation) with A/G-agarose beads (Santa Cruz Biotechnology) pre-linked with specific Abs (1 hr, 23° C.). The bound A/G beads were sequentially washed once with RIPA buffer, then twice with 0.5M LiCl and twice with Buffer A. The bound A/G bead sample, originated from the stimulated cells, was then incubated with Calf Intestinal Phosphatase (37° C., 1 hr, NEB, MA, USA) then washed. The samples were then resuspended in Buffer A containing 0.01% BSA and aliquoted-GST tagged proteins were incubated with beads (4° C., 2 hr), then washed and resuspended in sample buffer and boiled.

Subcellular Fractionation: Subcellular fractionation was performed as followed, harvested cells were resuspended in 200 µl of buffer H containing 0.1% Nonidet P-40. The lysates were mixed vigorously and centrifuged immediately as above to yield supernatants containing the cytosolic fraction. Nuclear proteins were extracted by resuspending the nuclear pellets in 200 µl of extraction buffer, waiting on ice for 5 min, brief sonication (2×5 sec, 40W, 4° C.), vigorous mixing, and centrifugation. The protein concentration was determined by Coomassie protein assay reagent (Pierce). Both cytosolic and nuclear fractions were subjected to Western blotting.

Gel filtration: HeLa cells were serum starved (as above) and then were either stimulated with anisomycin (Anis, 0.5 µg/ml, 15 min) and TPA (250 nM, 15 min), or left untreated (NT). Cell extracts (25 mg of each treatment) were loaded on a 16/60 superdex 200 sizing column (flow rate 1 ml/min), and 1 ml fractions were collected. The fractions were analyzed using Western blot with the appropriate Abs.

Statistical Analysis: Data are expressed as mean±S.E. Statistical evaluation was carried out using functional analysis and Student's t test (two-tailed) to test for differences between the control and experimental results. Values of $p<0.05$ were considered statistically significant.

In vivo experiment: 21 male C57BL mice were weighed then injected (I.V) with either peptide (15 mg/Kilo), scramble peptide (15 mg/Kilo) or DMSO (2%). Twenty-four hours post injection drinking water of the mice was replaced with water containing DSS (1.25%), peptide, scramble peptide or DMSO were injected every forty-eight hours. Mice were sacrificed seven days post replacement of drinking water, and colitis was assessed using endoscopy and weight of mice.

Results

The present inventors examined the intracellular distribution and stability of the myristoylated peptide using a FITC-conjugated myristoylated peptide, and found that the peptide efficiently penetrated the cells and remained in the cytoplasm even after 24 hrs (FIG. 16). Next we demonstrated the potential therapeutic usage of the peptide in a DSS-induced colitis model. Mice treated with the peptide demonstrated a reduced DSS-induced Colitis, compared with mice treated with control peptide (exhibited as average weight loss and number of lesions in the colon (FIGS. 17A-17C)). However, this peptide partially overlapped with the well-known kinase domain I, a conserve protein domain. To overcome this issue, the present inventors modified the peptide by substituting this region with Ala residues (FIGS. 18A-18B). They next demonstrated that this newly designed peptide inhibited the interaction of p38 with Imp7 and prevented the stimulation-induced nuclear translocation of JNK and p38 MAPKs without affecting the stimulation-dependent kinase activity of MAPKs (FIGS. 19-21).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated peptide comprising an amino acid sequence being at least 80% homologous to the sequence as set forth in SEQ ID NO: 1(PERYQNLSPV), the isolated peptide comprising a nuclear targeting activity, the peptide being no longer than 20 amino acids.

2. The isolated peptide of claim 1, being capable of preventing P38α nuclear translocation, the peptide being no longer than 20 amino acids.

3. The isolated peptide of claim 1, comprising the sequence as set forth in SEQ ID NO: 1 or SEQ ID NO: 8.

4. The isolated peptide of claim 1, wherein a heterologous substance is linked to said amino acid sequence via a linker.

5. The isolated peptide of claim 1, comprising the amino acid sequence as selected from the group consisting of SEQ ID NO: 2 (PERYQNLSPVG), SEQ ID NO: 3 (PERYQNLSPVGS), SEQ ID NO: 4 (PERYQNLSPVGSG) and SEQ ID NO: 5 (PERYQNLSPVGSGA), SEQ ID NO: 6 (KPERYQNLSPVGSGA) and SEQ ID NO: 7 (KPERYQNLSPVAAAA).

6. The isolated peptide of claim 1, being myristoylated.

7. A method of treating an inflammatory disorder or an immune disorder in a subject, the method comprising administering to the subject a therapeutically effective amount of the isolated peptide of claim 1 into the subject, thereby treating the inflammatory disorder or immune disorder.

8. The method of claim 7, wherein the immune disorder is an autoimmune disorder.

9. The method of claim 7, wherein the inflammatory disorder is colitis.

10. A composition of matter comprising the isolated peptide of claim 1 and a heterologous substance linked to said amino acid sequence via a linker.

11. A method of targeting a substance into a nucleus of a host cell, the method comprising introducing the substance into the host cell, the substance being attached to the peptide of claim 1.

12. A method of targeting a substance into a nucleus of a host cell, the method comprising introducing the peptide of claim 1 into the host cell, said peptide being linked to an affinity moiety capable of binding the substance.

13. A pharmaceutical composition comprising as an active agent the peptide of claim 1 and a pharmaceutically acceptable carrier.

14. The isolated peptide of claim 1, being lipidated.

* * * * *